US010737012B2

(12) United States Patent
Leach et al.

(10) Patent No.: US 10,737,012 B2
(45) Date of Patent: Aug. 11, 2020

(54) CELL WASHING USING ACOUSTIC WAVES

(71) Applicant: Biomet Biologics, LLC, Warsaw, IN (US)

(72) Inventors: Michael D. Leach, Warsaw, IN (US); Ned M. Hamman, Leesburg, IN (US); David Abeskaron, Warsaw, IN (US); Grant Cunningham, Warsaw, IN (US); Randel Dorian, San Diego, CA (US); Richard Wood Storrs, Berkeley, CA (US); Scott R. King, New Orleans, LA (US)

(73) Assignee: Biomet Biologics, Inc., Warsaw, IN (US)

( * ) Notice: Subject to any disclaimer, the term of this patent is extended or adjusted under 35 U.S.C. 154(b) by 65 days.

(21) Appl. No.: 15/217,635

(22) Filed: Jul. 22, 2016

(65) Prior Publication Data

US 2016/0325039 A1   Nov. 10, 2016

Related U.S. Application Data

(63) Continuation-in-part of application No. 14/674,089, filed on Mar. 31, 2015, now Pat. No. 9,855,382.
(Continued)

(51) Int. Cl.
*A61M 1/36* (2006.01)
*C12N 13/00* (2006.01)
(Continued)

(52) U.S. Cl.
CPC ........ *A61M 1/3692* (2014.02); *A61M 1/0281* (2013.01); *A61M 1/3678* (2014.02);
(Continued)

(58) Field of Classification Search
CPC .............. A61M 1/0281; A61M 1/3678; A61M 1/3692; A61M 2202/0429; A61M 2205/3375
See application file for complete search history.

(56) References Cited

U.S. PATENT DOCUMENTS 4,759,775 A   7/1988   Peterson et al.
5,039,426 A   8/1991   Giddings
(Continued)

FOREIGN PATENT DOCUMENTS

WO   WO-2013049623 A1   4/2013
WO   WO-2015061284 A1   4/2015
WO   WO-2016160261 A1   10/2016

OTHER PUBLICATIONS

Feuerborn, Terry. What Causes Brazil's Bizarre "Meeting of the Waters?" IFL Science! Accessed Nov. 5, 2019. Published Jul. 23, 2014. https://www.iflscience.com/environnnent/what-causes-brazil%E2%80%99s-bizarre-meeting-waters/.*
(Continued)

*Primary Examiner* — Adam Marcetich
(74) *Attorney, Agent, or Firm* — Schwegman Lundberg & Woessner, P.A.

(57) ABSTRACT

Disclosed is a device for separating a cellular component from a multicomponent fluid. The device can include a body, a first acoustic wave generator, and a second acoustic wave propagating component. The body can define a channel having a first surface, an opposing second surface, a first side, and an opposing second side. The channel can extend along a longitudinal axis from a first end to an opposing second end. The first acoustic wave generator can be coupled to the first surface. The second acoustic wave propagating component can be coupled to the second surface. The first acoustic wave generator and second acoustic
(Continued)

wave propagating component can be configured to generate a bulk standing acoustic wave in the channel.

20 Claims, 17 Drawing Sheets

Related U.S. Application Data

(60) Provisional application No. 62/196,339, filed on Jul. 24, 2015.

(51) Int. Cl.
| | |
|---|---|
| *C12N 5/078* | (2010.01) |
| *B01L 3/00* | (2006.01) |
| *B01L 9/00* | (2006.01) |
| *B01D 21/28* | (2006.01) |
| *A61M 1/02* | (2006.01) |
| *C12M 1/00* | (2006.01) |

(52) U.S. Cl.
CPC ...... *B01D 21/283* (2013.01); *B01L 3/502761* (2013.01); *B01L 9/527* (2013.01); *C12N 5/0641* (2013.01); *C12N 13/00* (2013.01); *A61M 2202/0429* (2013.01); *A61M 2205/3375* (2013.01); *B01L 2200/025* (2013.01); *B01L 2300/089* (2013.01); *B01L 2300/0874* (2013.01); *B01L 2300/0877* (2013.01); *B01L 2300/0887* (2013.01); *B01L 2400/0436* (2013.01); *C12M 47/02* (2013.01)

(56) References Cited

U.S. PATENT DOCUMENTS

| | | | |
|---|---|---|---|
| 5,225,089 A | 7/1993 | Benes et al. | |
| 5,613,456 A | 3/1997 | Kuklinski | |
| 5,688,405 A | 11/1997 | Dickinson et al. | |
| 5,834,625 A | 11/1998 | Kraus, Jr. et al. | |
| 5,895,362 A * | 4/1999 | Elstrom | A61B 5/14514 |
| | | | 600/573 |
| 8,535,536 B1 | 9/2013 | Gale et al. | |
| 9,855,382 B2 | 1/2018 | Leach et al. | |
| 2001/0055529 A1* | 12/2001 | Wixforth | B01F 11/0283 |
| | | | 417/53 |
| 2002/0007118 A1* | 1/2002 | Adachi | B06B 1/0611 |
| | | | 600/443 |
| 2002/0154571 A1 | 10/2002 | Cefai et al. | |
| 2004/0069717 A1* | 4/2004 | Laurell | A61M 1/3472 |
| | | | 210/748.05 |
| 2005/0100481 A1 | 5/2005 | Mae et al. | |
| 2005/0229696 A1 | 10/2005 | Takayama | |
| 2006/0037915 A1* | 2/2006 | Strand | B01D 21/283 |
| | | | 210/748.05 |
| 2006/0124555 A1 | 6/2006 | Nakatani | |
| 2006/0255323 A1* | 11/2006 | Seki | A61K 9/145 |
| | | | 252/519.21 |
| 2007/0000814 A1 | 1/2007 | Kennedy et al. | |
| 2007/0029257 A1 | 2/2007 | Mueth et al. | |
| 2007/0091442 A1 | 4/2007 | MacDonald et al. | |
| 2008/0085227 A1 | 4/2008 | Miyamoto et al. | |
| 2008/0181828 A1 | 7/2008 | Kluck | |
| 2009/0042239 A1 | 2/2009 | Ward et al. | |
| 2009/0139931 A1* | 6/2009 | Leonard | A61M 1/14 |
| | | | 210/645 |
| 2009/0158823 A1 | 6/2009 | Kaduchak et al. | |
| 2009/0178716 A1 | 7/2009 | Kaduchak et al. | |
| 2010/0137163 A1* | 6/2010 | Link | B01F 13/0071 |
| | | | 506/16 |
| 2011/0105982 A1 | 5/2011 | Leonard et al. | |
| 2011/0207238 A1 | 8/2011 | Horii et al. | |
| 2012/0106290 A1* | 5/2012 | Meijer | B01F 3/0861 |
| | | | 366/337 |
| 2013/0043170 A1 | 2/2013 | Rose et al. | |
| 2013/0135963 A1* | 5/2013 | Linne | B01F 5/0604 |
| | | | 366/337 |
| 2013/0175226 A1 | 7/2013 | Coussios et al. | |
| 2014/0133268 A1* | 5/2014 | Cornaglia | F01N 3/2892 |
| | | | 366/337 |
| 2014/0147860 A1 | 5/2014 | Kaduchak et al. | |
| 2014/0193381 A1 | 7/2014 | Warner et al. | |
| 2014/0311253 A1 | 10/2014 | Iwasa | |
| 2015/0025485 A1 | 1/2015 | Luckemeyer et al. | |
| 2015/0037863 A1* | 2/2015 | Bazou | C12N 5/0062 |
| | | | 435/173.1 |
| 2016/0139012 A1* | 5/2016 | D'Silva | G01N 1/34 |
| | | | 424/93.7 |
| 2016/0175742 A1 | 6/2016 | Abeskaron et al. | |
| 2016/0287778 A1 | 10/2016 | Leach et al. | |

OTHER PUBLICATIONS

"U.S. Appl. No. 14/674,089, Examiner Interview Summary dated Feb. 22, 2017", 3 pgs.
"U.S. Appl. No. 14/674,089, Final Office Action dated Mar. 20, 2017", 26 pgs.
"U.S. Appl. No. 14/674,089, Non Final Office Action dated Jan. 23, 2017", 22 pgs.
"U.S. Appl. No. 14/674,089, Response filed Mar. 6, 2017 to Non Final Office Action dated Jan. 23, 2017", 12 pgs.
"U.S. Appl. No. 14/674,089, Response filed Jun. 6, 2017 to Final Office Action dated Mar. 20, 2017", 12 pgs.
"U.S. Appl. No. 14/674,089, Response filed Oct. 3, 2016 to Restriction Requirement dated Sep. 26, 2016", 10 pgs.
"U.S. Appl. No. 14/674,089, Response filed Dec. 21, 2016 to Restriction Requirement dated Nov. 30, 2016", 9 pgs.
"U.S. Appl. No. 14/674,089, Restriction Requirement dated Sep. 26, 2016", 6 pgs.
"U.S. Appl. No. 14/674,089, Restriction Requirement dated Nov. 30, 2016", 7 pgs.
"U.S. Appl. No. 14/674,089, Non Final Office Action dated Jun. 20, 2017", 28 pgs.
U.S. Appl. No. 14/674,089, filed Mar. 31, 2015, Cell Washing Device Using Standing Acoustic Waves and a Phantom Material.
"International Application Serial No. PCT/US2016/020594, International Search Report dated May 31, 2016", 5 pgs.
"International Application Serial No. PCT/US2016/020594, Written Opinion dated May 31, 2016", 6 pgs.
"U.S. Appl. No. 14/674,089, Response filed Aug. 28, 2017 to Non Final Office Action dated Jun. 20, 2017", 11 pgs.
"International Application Serial No. PCT/US2016/020594, International Preliminary Report on Patentability dated Oct. 12, 2017", 8 pgs.
"U.S. Appl. No. 14/674,089, Notice of Allowance dated Oct. 16, 2017", 11 pgs.
"European Application Serial No. 16710579.0, Response filed May 11, 2018 to Action dated Nov. 14, 2017", 24 pgs.

* cited by examiner

CELL WASHING USING ACOUSTIC WAVES

RELATED APPLICATION

This application is a Continuation-In-Part of and claims the benefit of priority to U.S. patent application Ser. No. 14/674,089, filed on Mar. 31, 2015 and further claims the benefit of priority to U.S. Provisional Patent Application No. 62/196,339, filed Jul. 24, 2015, the content of which are hereby incorporated by reference in their entirety.

BACKGROUND

The present technology relates to separating components, such as red blood cells, from a mixture (such as a suspension), and particularly to separating a selected target component in a high concentration and purity using acoustic waves, such as bulk acoustic waves.

Blood transfusions are used to treat many disorders and injuries, such as in the treatment of accident victims and during surgical procedures. According to current American Red Cross statistics, about 5 million people receive blood transfusions each year, in the United States, alone. Thus, health care systems rely on the collection and distribution of blood. Typically, blood is obtained from a donor and then processed and stored; units of stored blood or blood products are then taken from storage as needed and transfused into a patient in need. In some cases, the blood may be an autologous donation, where an individual donates blood in expectation of receiving his or her own blood by transfusion during a medical procedure.

Donated blood is typically processed into components and then placed in storage until needed. When a subject is in need of a blood transfusion, a Unit of blood is commonly removed from storage, washed, and resuspended in an appropriate solution. The blood may also be treated with a red blood cell enhancement composition, to rejuvenate or improve aspects of red blood cell functionality, such as oxygen delivery capacity, that may be decreased during storage. In some instances, the red blood cells are lyophilized prior to storage, in which case they need to be resuspended, washed, and then resuspended again in an appropriate solution. The resuspended red blood cells are then transfused into the subject. In either scenario, washing the red blood cells is traditionally a tedious, time consuming and multistep process that requires a great deal of tubing, and the use of expensive centrifuges with rotating seals to separate the cells from the wash solution. Therefore, there remains a need to streamline and simplify the process for washing red blood cells prior to transfusion.

SUMMARY

To better illustrate the system disclosed herein, a non-limiting list of examples is provided here:

Example 1 can include a device for separating a cellular component from a multicomponent fluid. The device can comprise a body, a first acoustic wave generator, and a second acoustic wave propagating component. The body can define a channel having a first surface and a second surface opposite the first surface. The channel can extend along a longitudinal axis from a first end to a second end. The first acoustic wave generator can be coupled to the first surface. The first acoustic wave generator can be configured to generate an acoustic wave having a wavelength. The second acoustic wave propagating component can be coupled to the second surface. The second surface can be spaced an integer fractional multiple of the wavelength from the first surface and each integer factional multiple equals a number of pressure nodes within the channel.

In Example 2, the device of Example 1 can optionally include a central power generating region of the first acoustic wave generator being aligned with the second end of the channel and proximate a bifurcation region of the channel.

In Example 3, the device of any one of or any combination of Examples 1 and 2 can optionally include the integer fractional multiple being 0.5 and the number of pressure nodes is 1.

In Example 4, the device of any one of or any combination of Examples 1-3 can optionally include the first acoustic wave generator and the second wave propagating component being located proximate a midpoint of the channel.

In Example 5, the device of any one of or any combination of Examples 1-4 can optionally include the body comprises a phantom material forming at least a portion of one or both of the first surface and the second surface. The phantom material having acoustic properties similar to those of the multicomponent fluid and a thickness such that at least one of the pressure nodes is located proximate the phantom material.

In Example 6, the device of any one of or any combination of Examples 1-5, further comprising a first inlet and a second inlet proximate the first end, the first inlet having a higher elevation than the second inlet.

In Example 7, the device of Example 6 can optionally include a first outlet and a second outlet proximate the second end. The second outlet having a higher elevation than the first outlet.

In Example 8, the device of Example 7 can optionally include the first inlet being configured to receive a wash material and the second inlet is configured to receive a multicomponent mixture.

In Example 9, the device of Example 8 can optionally include the second outlet being arranged to receive the multicomponent mixture and the first outlet being arranged to receive the multicomponent mixture.

In Example 10, the device of any one of or any combination of Examples 1-9 can optionally include the channel having a cross-sectional width and height. An aspect ratio of width:height can be from about 1:11 to about 50:1. The first acoustic wave generator can produce waves having a frequency of from about 100 kHz to about 2000 kHz.

In Example 11, the device of any one of or any combination of Examples 1-10, can optionally include, during use, an antinode being formed at approximately the center of the channel and a first pressure node being formed at the first surface and a second pressure node being formed at the second surface.

Example 12 can include a device for separating a cellular component from a multicomponent fluid. The device can comprise a body, a first acoustic wave generator, and a second acoustic wave propagating component. The body can define a channel having a first surface and a second surface opposite the first surface. The channel can extend along a longitudinal axis from a first end to a second end. The channel can define a bifurcation region proximate the second end. The first acoustic wave generator can be coupled to the first surface. The first acoustic wave generator can be configured to generate an acoustic wave having a wavelength. The first acoustic wave generator can have a central power generating region aligned proximate the bifurcation region. The second acoustic wave propagating component can be coupled to the second surface. The second surface can be spaced a multiple of the half-wavelengths from the first surface such that, during use, an antinode is formed at approximately the center of the channel and a first pressure node is formed at the first surface and a second pressure node is formed at the second surface.

In Example 13, the device of Example 12 can optionally include the body comprising a phantom material forming at least a portion of one or both of the first surface and the second surface. The phantom material can have acoustic properties similar to those of the multicomponent fluid and a thickness such that at least one of the pressure nodes is located proximate the phantom material.

In Example 14, the device of any one of or any combination of Examples 12 and 13 can optionally include the first acoustic wave generator or the second wave propagating component being a resonator.

In Example 15, the device of any one of or any combination of Examples 12-14 can optionally include a first inlet and a second inlet proximate the first end. The first inlet can have a higher elevation than the second inlet.

In Example 16, the device of Example 15 can optionally include a first outlet and a second outlet proximate the second end. The second outlet can have a higher elevation than the first outlet.

In Example 17, the device of Example 16 can optionally include the first inlet being configured to receive a wash material and the second inlet being configured to receive a multicomponent mixture.

In Example 18, the device of Example 17 can optionally include the second outlet being arranged to receive the multicomponent mixture and the first outlet being arranged to receive the multicomponent mixture.

Example 19 can include a method of separating a cellular component from cellular component liquid stream. The method can comprise introducing the cellular component liquid stream and a wash material liquid stream into an acoustic wave separation device having a channel that defines a bifurcation region proximate a first outlet and a second outlet; contacting the cellular component liquid stream and the wash material liquid stream in the proximate a pressure node of a standing acoustic wave located proximate the bifurcation region thereby forcing the cellular component from the component liquid stream to the wash material liquid stream; and collecting the wash material liquid stream in the first outlet.

In Example 20, the method of Example 19 can optionally include the standing acoustic wave being a surface acoustic wave.

In Example 21, the devices or methods of any one of or any combination of Examples 1-20 are optionally configured such that all elements or options recited are available to use or select from.

Further areas of applicability will become apparent from the description provided herein. The description and specific examples in this summary are intended for purposes of illustration only and are not intended to limit the scope of the present disclosure.

DRAWINGS

The accompanying drawings, as briefly summarized below, depict exemplary embodiments of the present technology.

Figure 12:
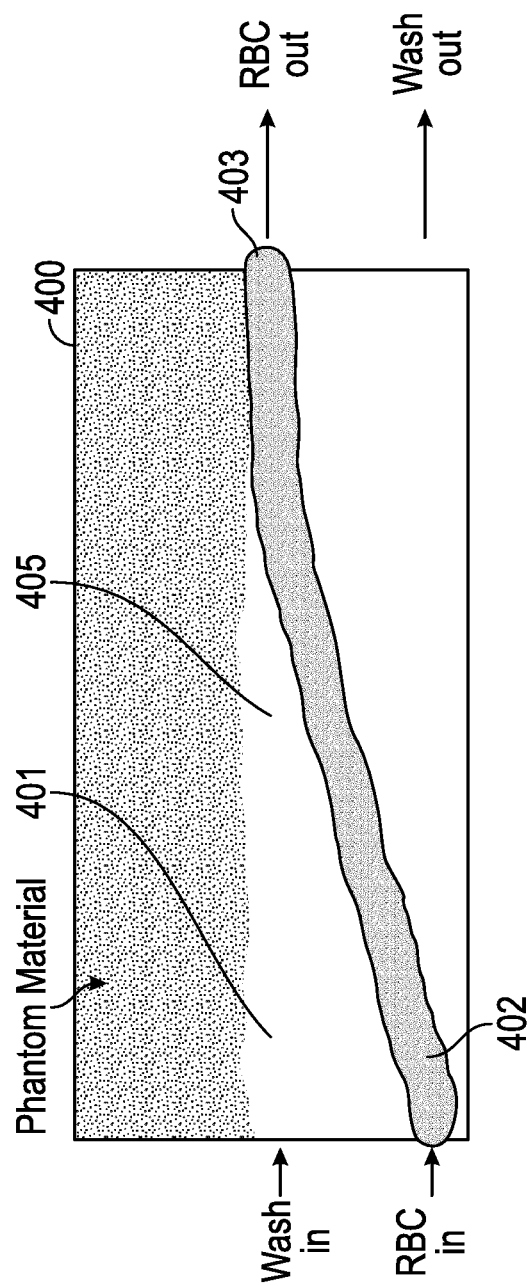
Figure 13A:
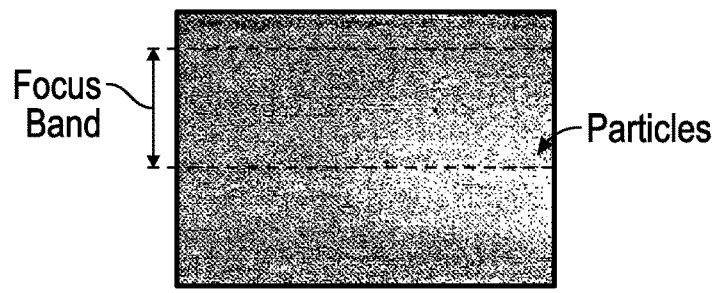
Figure 13B:
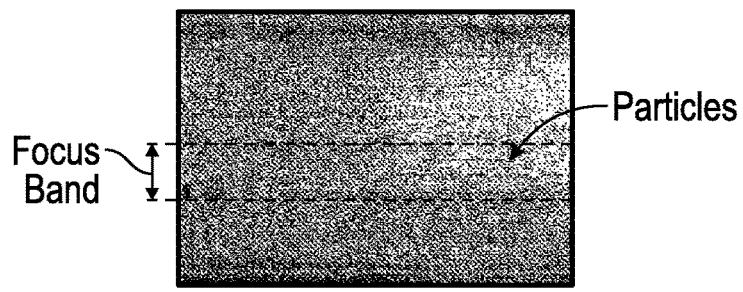
Figure 13C:
Figure 13D:
Figure 13E:
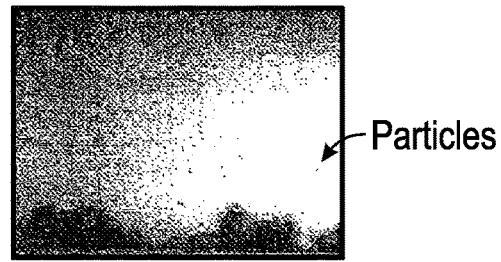
Figure 14A:
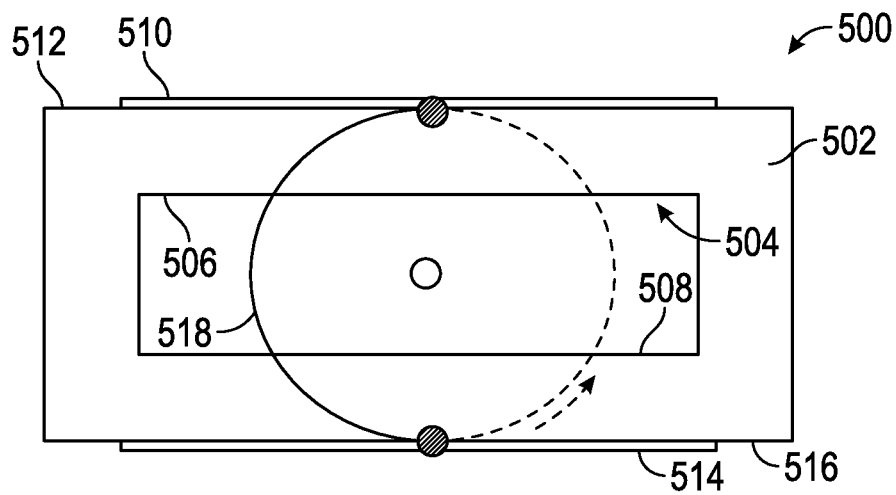
Figure 14B:
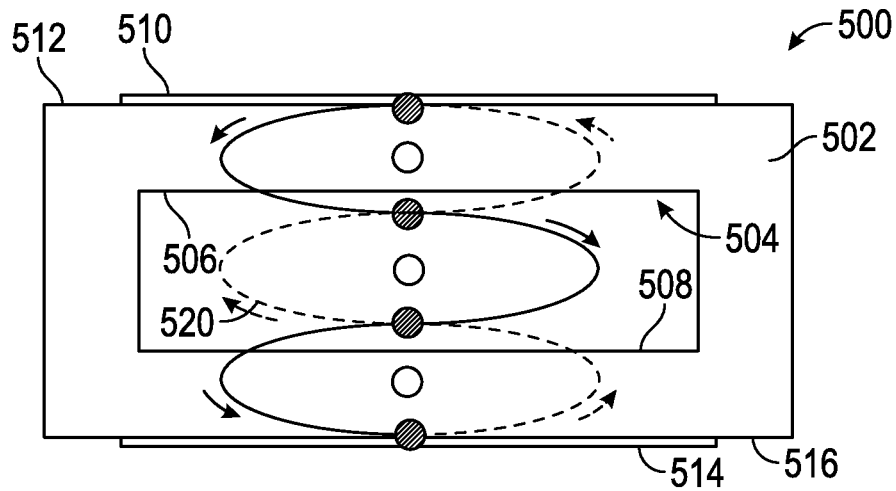
Figure 14C:
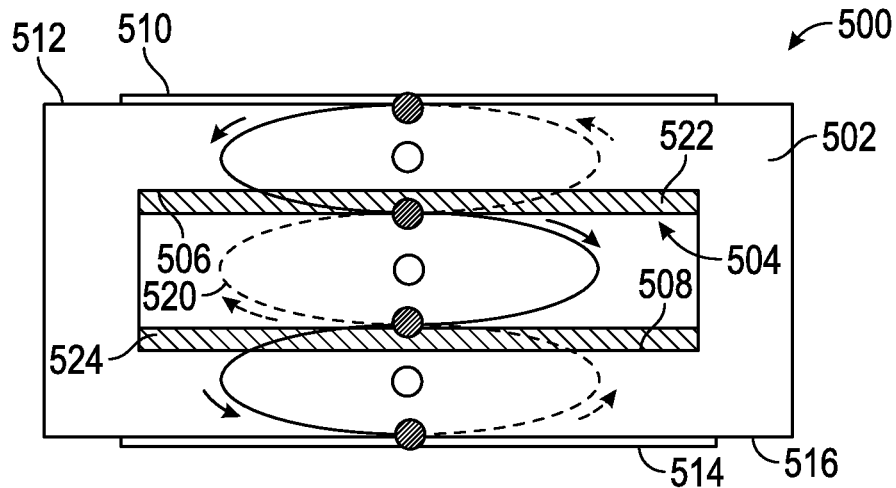

FIG. 12 is a diagram of a device for washing multicomponent mixtures according to the present technology; and FIGS. 13A-13E are photographs showing bands of particles formed by flowing through standing acoustic waves located within channels of a device of the present technology; and FIGS. 14A-14C are graphic illustrations showing cross-sections of chips defining channels, wherein standing acoustic waves are generated across the channels.

Figure 15:
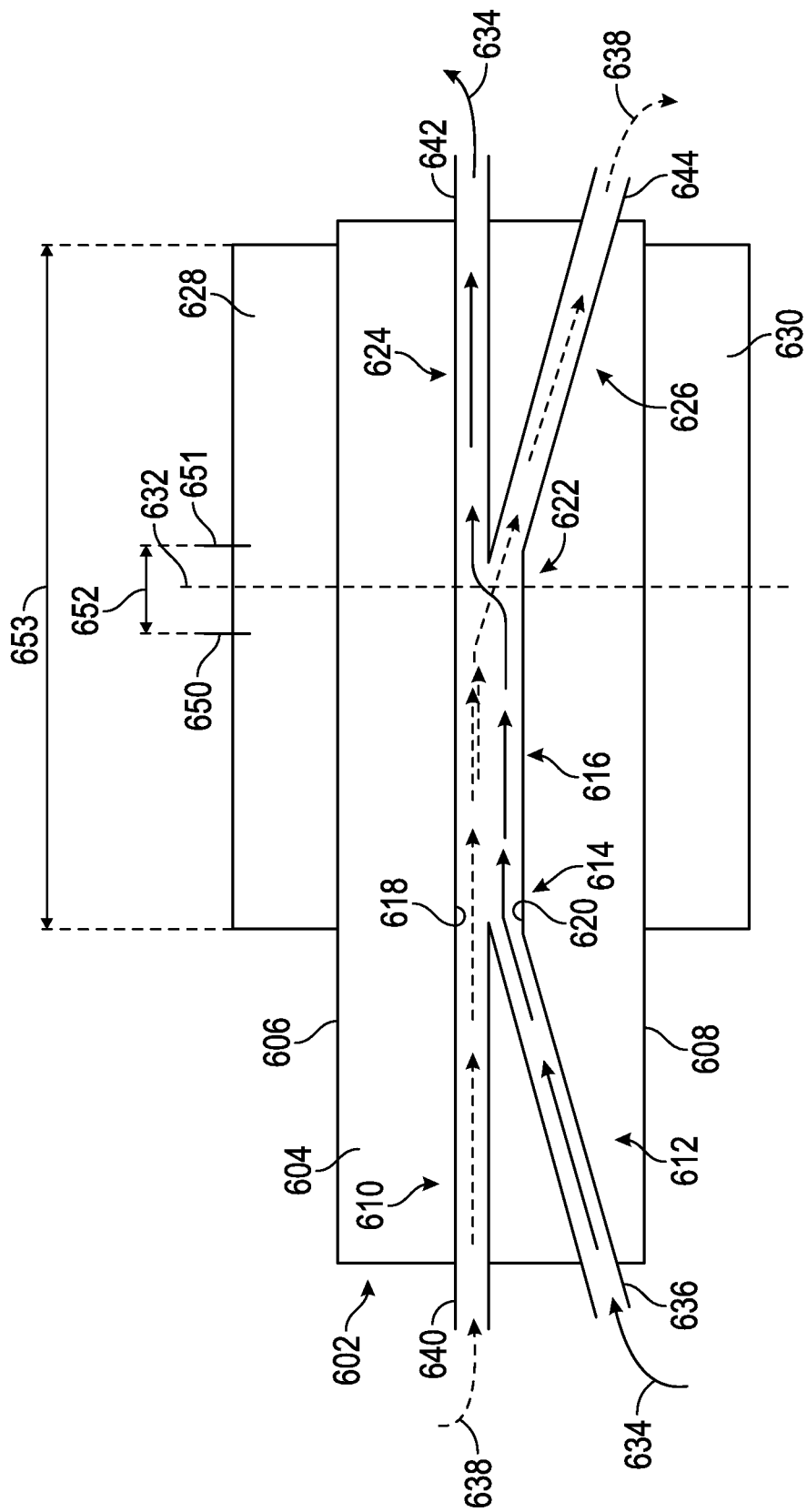

FIG. 15 is a graphic illustration of a chip of the present technology.

Corresponding reference numerals indicate corresponding parts throughout the several views of the drawings. It should be noted that the figures set forth herein are intended to exemplify the general characteristics of materials, compositions, devices, and methods among those of the present technology, for the purpose of the description of certain embodiments and are not intended to limit the scope of the present disclosure. These figures may not precisely reflect the characteristics of any given embodiment, and are not necessarily intended to fully define or limit specific embodiments within the scope of this technology.

DETAILED DESCRIPTION

The following description of technology is merely exemplary in nature of the composition, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

Although traditional methods for washing blood are largely effective, there remains a need to streamline the process for isolating blood cells from multicomponent fluids. It has been found that processing and washing blood may be performed using standing acoustic waves (SAWs), also referred to as stationary waves. Generally, standing waves are created by the interference between two intersecting sinusoidal waves having essentially identical frequencies, formed in a liquid or other medium. For example, opposing waves can be propagated laterally, parallel to the flow path in a channel through which fluid flows, creating an interfering standing acoustic wave pattern in the fluid. Such waves may be referred to as surface acoustic waves. Alternatively, opposing acoustic waves may be propagated on opposite sides of the channel (e.g., from the top and bottom, or from opposite ends) to form interfering standing wave patterns in the reservoir that may be referred to as bulk acoustic waves.

In both surface and bulk acoustic waves, pressure nodes and antinodes are formed in the fluid that can be used to manipulate a target particulate or other solid or semi-solid component, such as red blood cells, that is in the fluid. In particular, a pressure node of a SAW may be used to force a cell or other component in the fluid to a location within a fluid reservoir, based on the component's acoustical, physical, and mechanical properties. The present technology provides devices, systems and methods using SAWs to separate target components, such as cells, from multicomponent fluids. In some embodiments, the SAWs are surface acoustic waves. In various other embodiments, the SAWs are bulk acoustic waves.

In particular, the present technology provides devices (chips), systems, and methods for separating a component from a multicomponent fluid. As further described below, the devices comprise a channel or other reservoir in which the multicomponent fluid flows or is contained, wherein two or more wave propagating components are disposed on one or more surfaces of the reservoir, in acoustic communication with the reservoir. The wave propagating components generate standing acoustic waves that include pressure nodes and antinodes in the fluid.

Wave Propagating Components:

The devices and systems of the present technology comprise at least one acoustic wave generator, and a second wave propagating component. Wave generators suitable for use in the present technology include acoustic wave generators among those known in the art. In various embodiments, acoustic wave generators comprise piezoelectric transducers, which convert electrical pulses to mechanical vibrations. Non-limiting examples of piezoelectric materials include quartz, quartz crystal, ceramic, ceramic composites, berlinite ($AlPO_4$), lead titanate ($PbTiO_3$), barium titanate ($BaTiO_3$), lead zirconate titanate ($Pb[Zr_xTi_{1-x}]O_3$, $0 \leq x \leq 1$; "PZT"), potassium niobate ($KNbO_3$), lithium niobate ($LiNbO_3$), lithium tantalate ($LiTaO_3$), sodium tungstate ($Na_2WO_3$), $Ba_2NaNb_5O_5$, $Pb_2KNb_5O_{15}$, zinc oxide (ZnO), sodium potassium niobate (($K,Na)NbO_3$), bismuth ferrite ($BiFeO_3$), sodium niobate ($NaNbO_3$), bismuth titanate ($Bi_4Ti_3O_{12}$), sodium bismuth titanate ($Na_{0.5}Bi_{0.5}TiO_3$), and polymers, such as polyvinylidene fluoride (PVDF). In various embodiments, the wave generators are operated at a frequency of from about 100 kHz to about 2000 kHz, from about 300 kHz to about 1000 kHz, from about 400 kHz to about 900 kHz, from about 500 kHz to about 800 kHz, or from about 600 kHz to about 700 kHz. In one embodiment, the frequency is from about 680 kHz to about 710 kHz.

In some embodiments, such as in devices for producing surface acoustic waves, the acoustic wave generator is an interdigital or interdigitated transducer (IDT), comprising interlocking comb-shaped arrays of electrodes disposed on the surface of a piezoelectric substrate. In some embodiments, such as for producing bulk acoustic waves, the acoustic wave generator comprises a monolithic ceramic piezoelectric material in a thin-film transducer, such as a thickness shear mode resonator (TSMR).

Second wave propagating components useful herein include acoustic wave generators (i.e., a second acoustic wave generator, as described above) and acoustic reflectors. Reflectors comprise acoustically reflective materials or surfaces, such as a slide, layer or membrane composed of glass, polymer, plastic, metal, or ceramic that is substantially reflective to acoustic waves. It will be appreciated that the reflectivity of the material may be a function of the density of the material relative to the fluid through which waves are propagated, as well as the frequency of the waves. As non-limiting examples, the reflective material can be biaxially-oriented polyethylene terephthalate (boPET) polyester film (such as Mylar® brand BoPET commercialized by DuPont; Wilmington, Del.), glass mica, polymers, or a combination thereof.

As briefly discussed above, devices of the present technology create standing acoustic waves by positioning an acoustic wave generator in proximity to a second wave propagating component, in a fluid reservoir substrate (e.g., a fluid channel), so as to create an interfering wave pattern in the fluid reservoir. For example, by positioning first and second wave generators, such as piezoelectric transducers, opposite each other on a substrate, a SAW can be generated when acoustic waves from each generator interfere with each other. Alternatively, a SAW can be generated by positioning a wave generator on one side of a substrate and positioning a reflective material (as the second wave propagating component) on a side of the substrate opposite the wave generator. By adjusting the distance between the wave generators (or wave generator and reflective surface) and/or by adjusting the frequencies of the acoustic waves, the position of a pressure node associated with a SAW can be manipulated, located and controlled, for example, within a channel positioned between the wave generators (or wave generator and reflective surface). As discussed further below, the position of the acoustic wave in the fluid is determined by the frequency of the wave and the dimensions of the reservoir (e.g., a channel), containing the fluid.

For example, FIGS. 14A-14C depict a cross-section of a chip 500 having a body 502 that defines a channel 504. The channel 504 has a channel ceiling 506 and an opposing channel floor 508. A first wave generator 510 is positioned on an upper surface 512 of the chip 500 and a second wave generator 514 is positioned on an opposing lower surface 516 of the chip 500. However, it is understood that a combination of a wave generator and an opposing reflective material or surface can also be utilized. In FIG. 14A, the wave generators 510, 514 are tuned to generate a SAW 518 with a wavelength of 0.5λ. In this embodiment, the nodes, shown as filled-in circles, would push flowing cells toward the antinode, shown as an open circle. In FIG. 14B, the wave generators 510, 514 are tuned to generate a SAW 520 with a wavelength of 1.5λ having two nodes and one antinode positioned in the channel 504. Here, cells flowing through the channel 504 would be pushed away from the nodes towards the antinode in the center of the channel 504 and towards the antinodes within the chip body 502. Therefore, if it is desired to direct cells toward the antinode in the center of the channel 504, either a new chip can be manufactured with a channel having a different size or the current channel 504 can be modified.

As discussed above, the frequency of the wave generator (s) can vary, for example ranging from about 100 kHz to about 2000 kHz. The specific frequency may be determined in conjunction with the dimensions of the channel or other reservoir in which the standing wave is to be created, so as to produce pressure nodes in the desired locations. The position of a pressure node or antinode associated with a SAW in a chip is dependent on the thickness of the chip materials in between the wave generators (or between a wave generator and a reflective surface) and the speed of sound in the chip material. Thus, the fluid reservoir (channel) dimensions are preferably optimized in regard to the frequency of the wave generator. For example, whereas low frequencies can support large channel dimensions, high frequencies are typically used with small channel dimensions. Therefore, depending on the frequency of the wave generators, the chips of the present technology comprise channels having a cross-sectional aspect ratio (width:height) of from about 1:1 to about 50:1 or from about 1:1 to about 40:1, or from about 1:1 to about 30:1, or from about 1:1 to about 20:1, or from about 1:1 to about 10:1, or from about 1:1 to about 5:1. Moreover, the input voltage of the wave generators can be from about 1 V to about 120 V and is dependent on chip geometry, hematocrit, and flow rate.

As stated above, the wave propagating devices are disposed on the surface of the device reservoir, so as to be in acoustic communication with the multicomponent fluid in the reservoir. In embodiments comprising a channel, having a fluid inlet at a first end and a fluid outlet at the opposite second end, through which the fluid flows, the wave propagating devices may be disposed at any point laterally along a surface of the channel, parallel to the axis of fluid flow. In some embodiments, a first wave generator and a second fluid propagating component (a second wave generator or a reflector) may be essentially in the mid-point of the channel, between the inlet and outlet. In other embodiments, the wave generator and second fluid propagating component are disposed near the outlet of the channel. It has been found that, in some embodiments wherein the fluid propagating components are disposed near the outlet, cells in the multicomponent fluid may be disposed in the fluid more easily and using less power than in embodiments where the wave propagating components are disposed at or near the mid-point of the channel. It will be appreciated that the precise special orientation of a wave propagating component near the outlet of the channel will be affected by the length of the channel (i.e, in the dimension parallel to the fluid flow) and the size of the wave propagating component. In various embodiments, the mid-point of the wave propagating component is within 10%, within 20%, or within 30% of the outlet, as a percentage of the distance between the inlet and outlet.

In some embodiments, such as the chip 602 depicted in FIG. 15 (which is further discussed below), a wave propagating component 628 comprises a central power generating region, defined by a first end point 650 and a second end point 651 on the longitudinal surface (e.g., top surface 606) of the chip 602. The length of the central power generating region, i.e., the distance 652 between the first end point 651 and the second end point 652, consists of the middle 20%, 10% or 5% of the wave propagating component, as a percentage of the overall length 653 of the wave propagating component (i.e., the dimension that is parallel to the flow of fluid in the channel). In various embodiments, a point within the central power generating region of the wave propagating component is axially aligned with the outlet end (second end, as discussed above) of the separation channel. That is, in reference to FIG. 15, both a point that is within the central power generating region of the wave propagating component, and the outlet end 622 of the separation channel 616, fall on a common axis 632 that is orthogonal to a surface (e.g., ceiling 618) of the channel. In some embodiments, the second end point 651 of the central power generating region is axially aligned with the outlet end 622 of the separation channel 616.

Devices

The present technology provides devices, such as fluidic chips, that comprise a channel or other reservoir in which standing acoustic waves may be used so as to apply forces to cell in a multicomponent fluid. As discussed above, such forces may be used to move the cells in the fluid, such as by forcing cells from the fluid into a second fluid within the device. In various embodiments, such movement of cells from a first multicomponent fluid effects washing of the cells, thereby creating a suspension of cells in a second fluid The chips may be constructed of any of a variety of materials, including such materials known in the art. The materials are preferably compatible with physiological materials (e.g., blood cells) that are processed with the devices, and have appropriate acoustic characteristics. Examples include polyethylene terephthalate (PET) acrylics, such as poly(methyl methacrylate) (PMMA), and glasses.

Figure 1A:
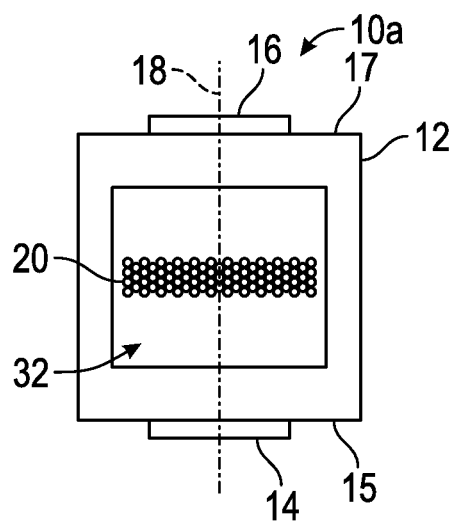
FIG. 1A is a schematic illustration of a cross section of a device configured to generate a standing acoustic wave.

FIG. 1A shows a cross-sectional view of an exemplary device 10*a* comprising a substrate or device body 12, a first wave component 14, and a second wave component 16 positioned on opposite sides 15, 17 of the body 12, wherein the body 12 defines a channel 32 with a square cross-sectional geometry. As discussed above, the first wave component 14 and the second wave propagating component 16 are individually either a wave generator or a reflective material or reflective surface or layer. However, when one of the wave components 14, 16 is a reflective material or reflective surface or layer, the other wave component 14, 16 is a wave generator. Alternatively, a side 15, 17 of the device body 12 can be composed of a reflective material so long as the opposite side 15, 17 comprises a wave generator. A SAW is generated between the first wave component 14 and the second wave component 16 along line 18. A pressure node associated with the SAW, which is located within the channel 32, forces a plurality of cells 20 into a plane perpendicular to the line 18.

Figure 1B:
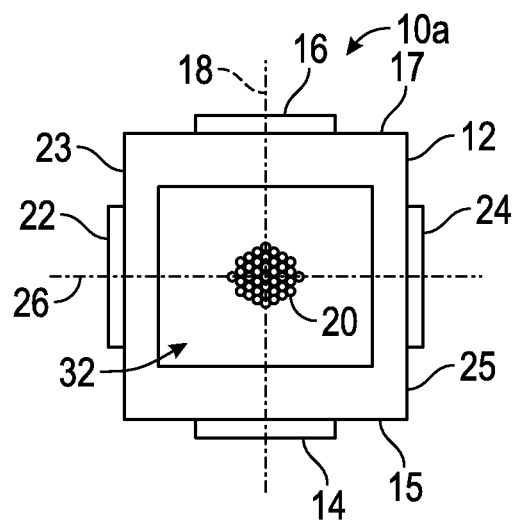
FIG. 1B is a schematic illustration of a cross section of a device configured to generate a pair of standing acoustic waves orthogonal to each other.

FIG. 1B shows a cross-sectional view of another exemplary device 10*b*, which is similar to device 10*a*. However, the device 10*b* further comprises a third wave propagating component 22 and a fourth wave propagating component 24 positioned on opposite sides 23, 25 of the body 12. The third wave component 22 and the fourth wave component 24 are individually either a wave generator or a reflective material or reflective surface or layer. However, when one of the wave components 22, 24 is a reflective material or reflective surface or layer, the other wave component 22, 24 is a wave generator. The third wave component 22 and the fourth wave component 24 are positioned orthogonal to the first wave component 14 and the second wave component 16 on sides 23, 25 of the body 12. A first SAW is generated between the first wave component 14 and the second wave component 16 along line 18 and a second SAW is generated between the third wave component 22 and the fourth wave component 24 along line 26 that is orthogonal to the first line 18, such that the second SAW is orthogonal to the first SAW. Pressure nodes associated with the SAWs interest with each other and interact with the plurality of cells 20 in orthogonal directions to force the cells 20 into a linear configuration, as shown more clearly in FIG. 3.

Figure 2:
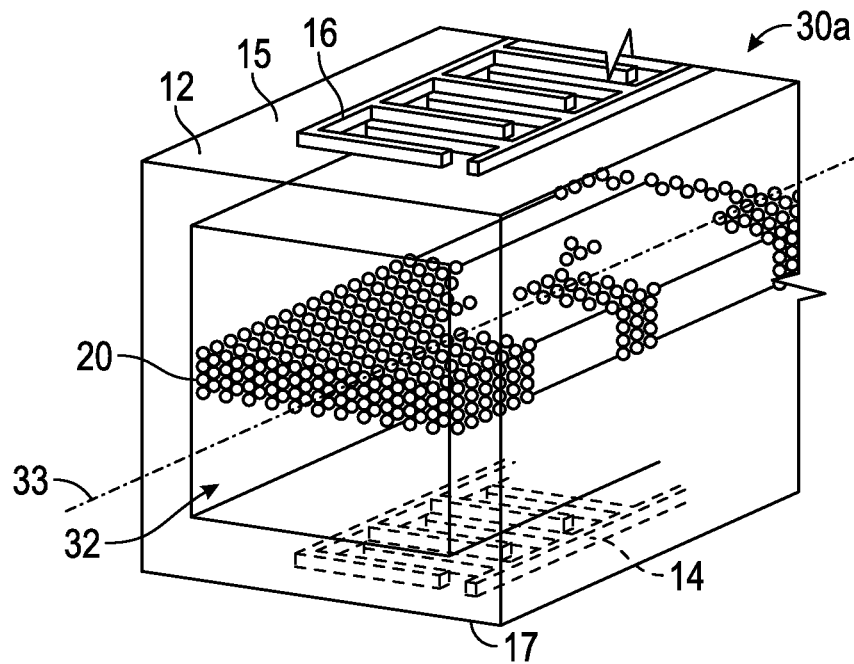
FIG. 2 is a perspective illustration of cells flowing through a channel, the cells interacting with a single standing acoustic wave.

FIG. 2 provides a perspective view of a device 30a, which is similar to the device 10a. The device 30a comprises a substrate or device body 12, a first wave component 14, and a second wave component 16 positioned on opposing sides 15, 17 of the body 12. As shown in FIG. 2, the first and second wave components 14, 16 are wave generators. The device 30a comprises a longitudinal channel 32 with a square cross-sectional geometry that extends along a longitudinal axis 33. As shown in FIG. 2, the cells 20 are suspended in a plane that extends along the axis 33 and that is parallel to the wave components 14, 16 by a pressure node associated with a SAW generated by the first wave component 14 and the second wave component 16.

Figure 3:
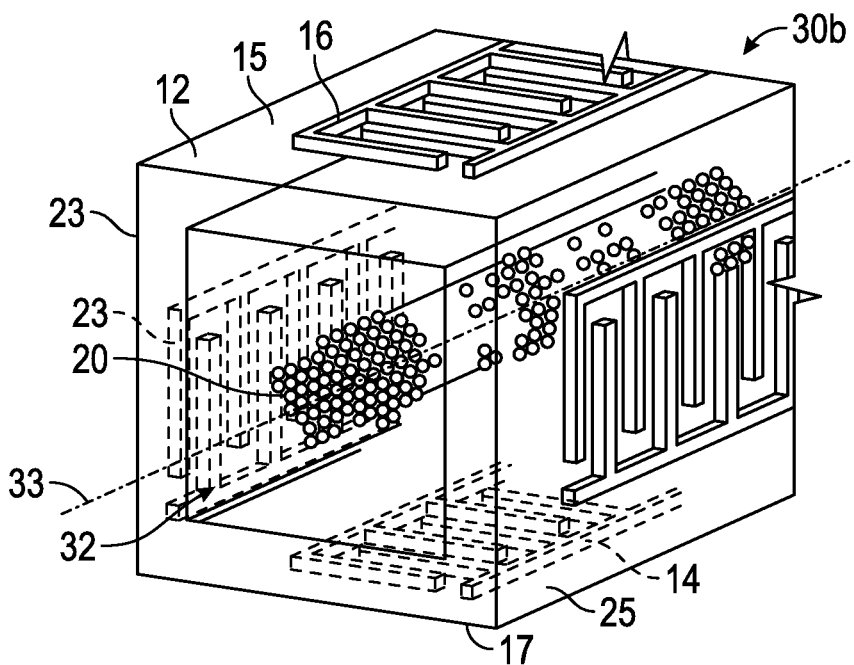
FIG. 3 is a perspective illustration of cells flowing through a channel, the cells interacting with a pair of orthogonal standing acoustic waves.

FIG. 3 provides a perspective view of another exemplary device 30b, which is similar to the device 10b. The device 30b comprises a substrate or device body 12, a first wave component 14 and a second wave component 16 positioned on opposing sides 15, 17 of the body 12, and a third wave component 22 and a fourth wave component 24 positioned on opposing sides 23, 25 of the body 12 that are orthogonal to the sides 15, 17 that include the first and second wave components 14, 17. Again, the device 30b comprises a longitudinal channel 32 with a square cross-sectional geometry that extends along the axis 33. As shown in FIG. 3, the cells 20 are suspended in a cylindrical line along the axis 33 of the channel 32 by a first pressure node associated with a first SAW generated by the first wave component 14 and the second wave component 16 and by a second pressure node associated with a second SAW generated by the third wave component 22 and the fourth wave component 24, wherein the second SAW is orthogonal to the first SAW.

Figure 1C:
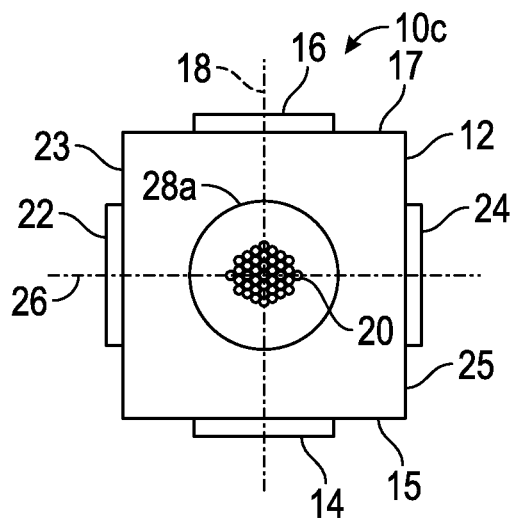
FIG. 1C is a schematic illustration of a cross section of device comprising a centered channel, the device configured to generate a pair of standing acoustic waves orthogonal to each other.
Figure 1D:
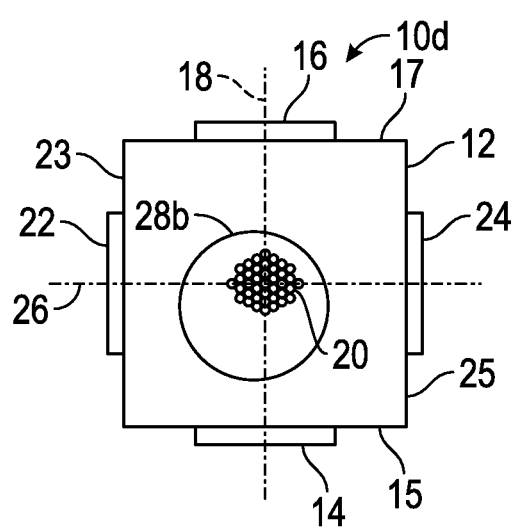
FIG. 1D is a schematic illustration of a cross section of device comprising an offset channel, the device configured to generate a pair of standing acoustic waves orthogonal to each other.

Referring now to FIG. 1C, a device 10c is shown, which is similar to device 10b. However, device 10c further comprises a channel 28a with a circular cross-sectional shape. Because the channel 28a is centered in the substrate 12, and because the wave components 14, 16, 22, 24 are centered on their respective sides of the substrate 12, the cells 20 are suspended in a line central to the channel 28a. As shown in FIG. 1D, a device 10d comprises a channel 28b, which is offset relative to the center of the substrate 12. The cells 20 are positioned in a line extending along a midpoint of a cross-section of the substrate 12 because the pressure nodes force the cells 20 to that position. In other words, the cells 20 are positioned based upon the pressure node or nodes and not upon the positioning of the channel 28a, 28b, 32.

In various embodiments, channels or other reservoirs may comprise a phantom material so as to alter the flow of fluid within the reservoir relative to the SAW and, in some embodiments, inlet and outlet regions of the device. As used herein, a "phantom material" is a material that mimics the acoustic properties of the fluid through which acoustic waves are propagated. In various embodiments, the phantom material mimics the acoustic properties of water with a low attention coefficient. Therefore, an acoustic wave travels through phantom materials substantially as it would, such as with the same speed, through water. For example, sound travels through water at a rate of from about 1450 m/s to about 1570 m/s. Similarly, sound travels through the phantom materials at a rate of from about 1200 m/s to about 1600 m/s, or at a rate of from about 1400 m/s to about 1500 m/s. Non-limiting examples of suitable phantom materials include Solid Water® phantom material from CNMC Co. Inc. (Nashville, Tenn.), Virtual Water™ phantom material from CNMC Co. Inc., and Plastic Water® phantom material from Computerized Imaging Reference Systems, Inc. (Norfolk, Va.). Various plastics, acrylics, and glasses detrimentally affect how acoustic waves travel. Because phantom materials do not affect how an acoustic wave travels, separation devices with complex geometries, such as single chips or devices having multiple channels, can be generated. Therefore, phantom materials may be included in channels to alter a flow path without affecting the position of an acoustic node or antinode. Additionally, in some embodiments, two or more devices of the current technology may be multiplexed to reduce surface area and to increase efficiency.

For example, the devices 10a, 10b, 10c, 10d shown in FIGS. 1A-1D comprise, at least partially, a phantom material. Similarly, FIG. 14C, depicts a device having channels comprising a phantom material. In particular reference to FIG. 14C, the channel 504 may comprise a first sheet of phantom material 522 along the ceiling 506 of the channel 504 and a second sheet of phantom material 524 along the floor 508 of the channel 504. The SAW 520 travels through phantom materials substantially as it would, such as with the same speed, through water. Therefore, placement of the sheets of phantom material 522, 524 does not affect the location of the nodes and antinodes. By using the sheets of phantom materials 522, 524, nodes can be located at interfaces between the sheets of phantom materials 522, 524 and the channel 504 so that the nodes force cells only towards the antinode in the center of the channel 504. In other words, phantom materials can be used to manipulate the dimensions of the channel 504 without affecting the location of the nodes generated by the SAW 520. Further exemplary chip and separation embodiments are provided below.

Figure 4:
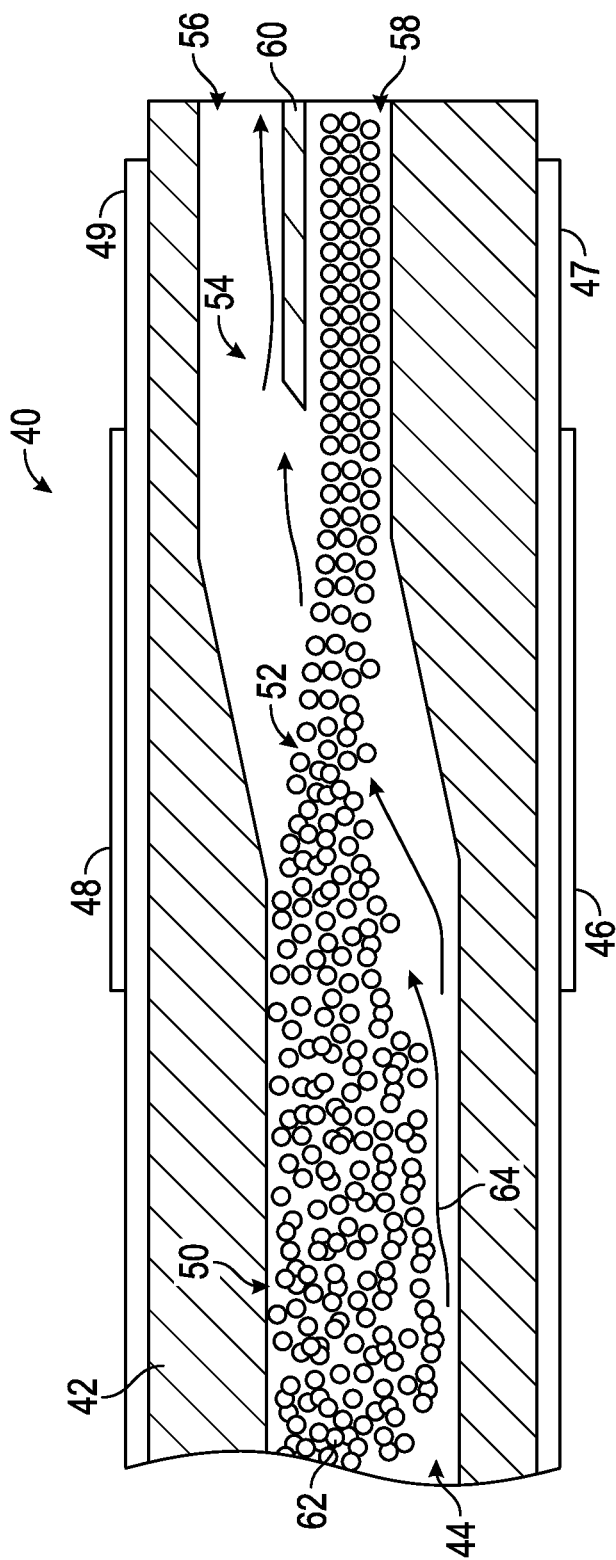
FIG. 4 is a cross-sectional representation of cells flowing through a device according to the present technology.

FIG. 4 shows a cross-section view of another exemplary device 40 for washing a multicomponent mixture comprising cells, such as, for example, red blood cells. The device 40 comprises a body 42 defining a channel 44, a first wave component 46 positioned on or near a first side 47 of the body 42 and a second wave component 48 positioned opposite to the first wave component 46 on or near a second opposing side 49 of the body 42. The first wave component 46 and the second wave component 48 are individually either a wave generator or a reflective material or reflective surface or layer. However, when one of the wave components 46, 48 is a reflective material or reflective surface or layer, the other wave component 46, 48 is a wave generator. A SAW is generated between the first wave component 46 and the second wave component 48 such that a pressure node is located within the channel 44. The channel 44 comprises a first horizontal section 50, a second connecting section 52, and a third horizontal section 54, such that the first horizontal section 50 is offset from the second horizontal section 54. The third section 52 is bifurcated into a first collection channel 56 and a second collection channel 58 by a planar shelf 60 defined by the body 42. The wave components 46, 48 are positioned on the first side 47 and on the second opposing side 49 of the body 42, respectively, which are parallel to the channel 44 at the connecting section 52 and the second horizontal section 54, such that the channel 44 is positioned between the first and second wave components 46, 48. In this embodiment, the wave propagating components 46, 48 (e.g., wave generators) are positioned close to the collection channel 58 to promote efficient separation. When a multicomponent mixture comprising red blood cells 62 and a wash material 64 are introduced into the device 40, they mix at the first lower horizontal section 50. However, upon reaching the pressure node, the red blood cells 62 are forced into a plane at the connecting section 52 corresponding to a pressure antinode. Simultaneously, the wash material, flow thereof represented by arrows 64, passes through the red blood cells 62, thereby washing the red blood cells 62. The red blood cells 62 are then collected from the second collection channel 58 and the wash material 64 and other waste is collected from the first collection channel 56. In other embodiments, the multicomponent mixture comprising red blood cells 62 and the wash material 62 are mixed prior to being introduced into the device 40.

Figure 5:
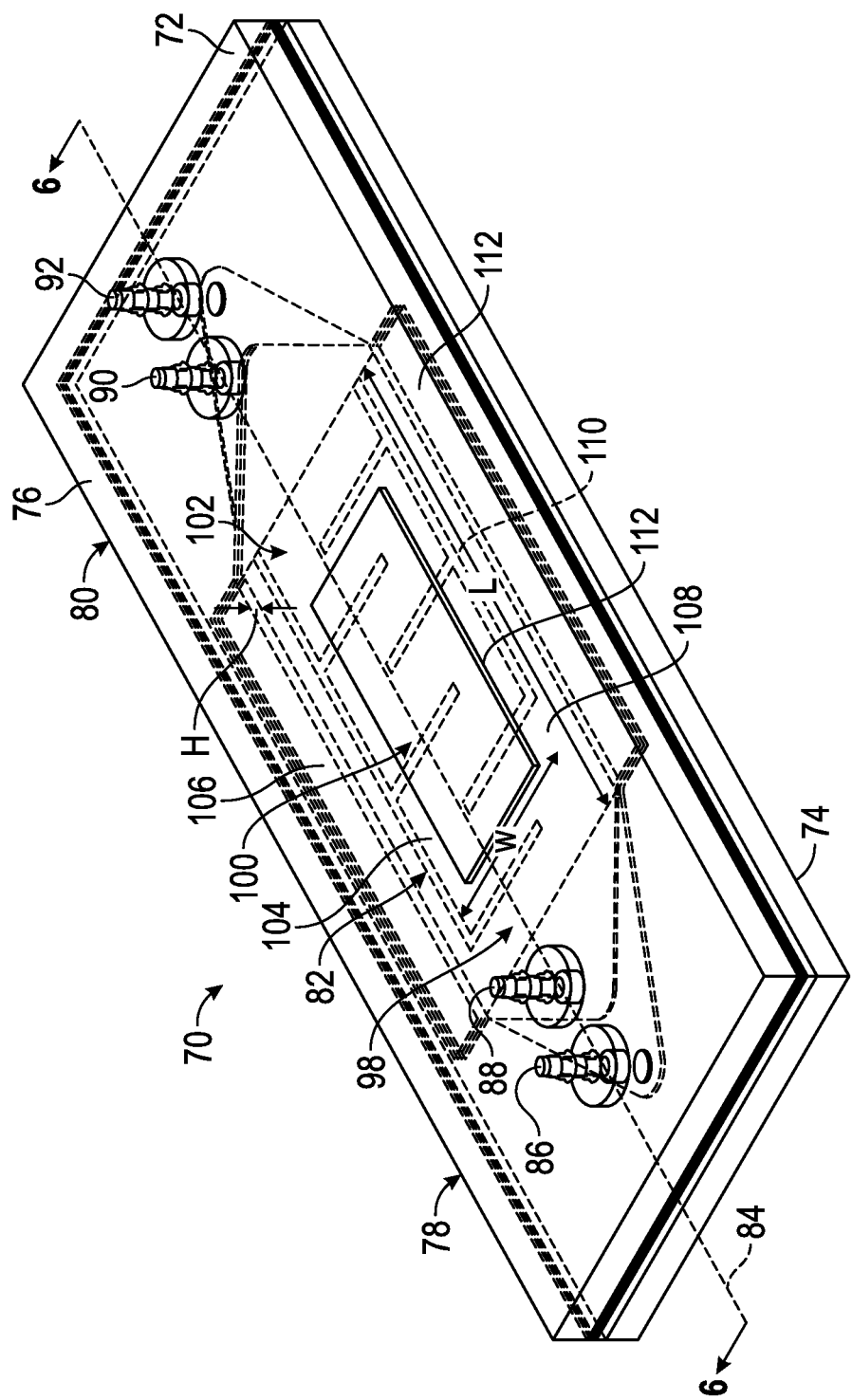
FIG. 5 is a perspective illustration of a device according to the present technology.
Figure 6A:
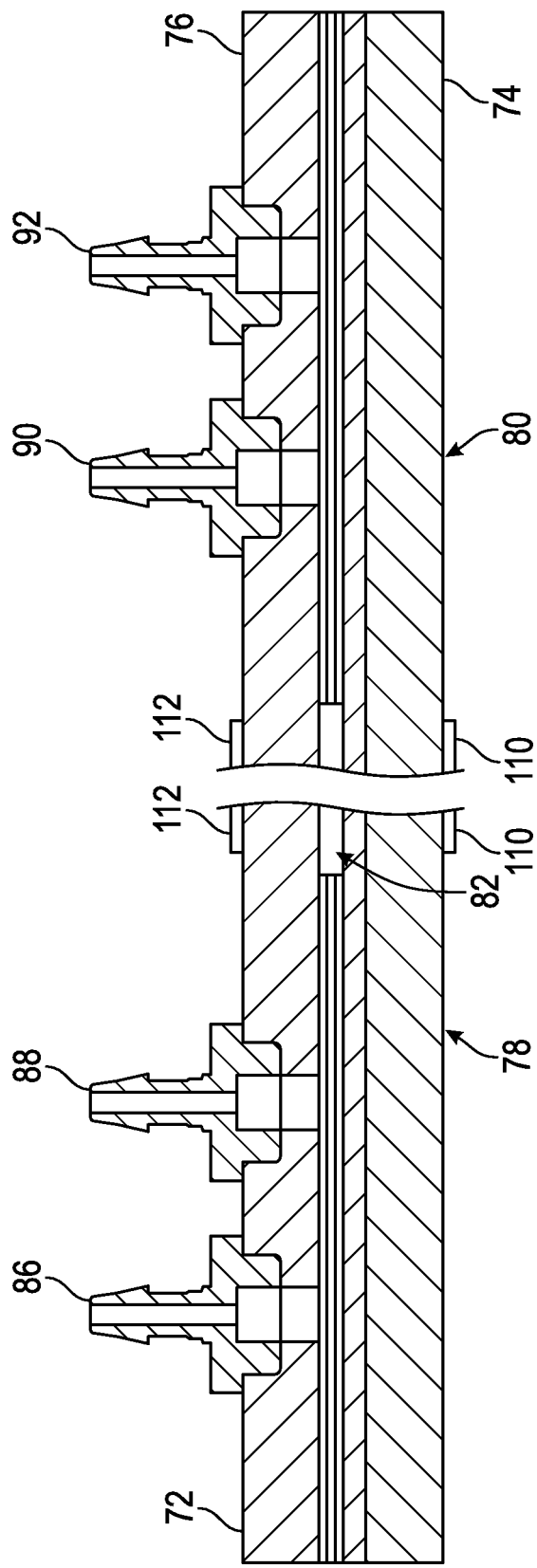
FIG. 6A is a cross-sectional perspective of the device of FIG. 5 taken along line 6A.
Figure 6B:
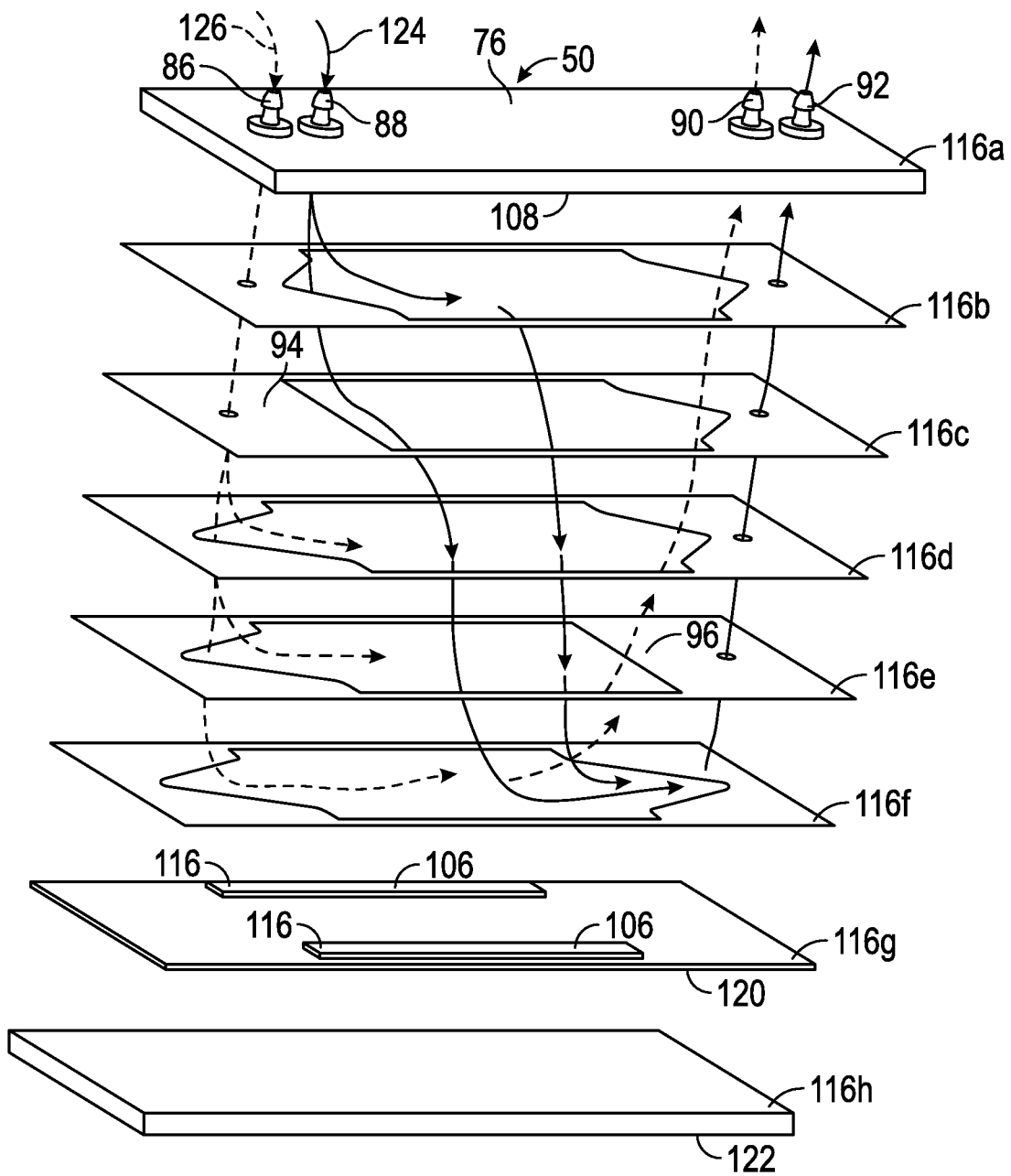
FIG. 6B is an exploded view of a plurality of layers that combine to form the device shown in FIGS. 5 and 6A.

FIG. 5, depicts another exemplary device a device 70 for washing a multicomponent mixture. The device 70 comprises a body 72 having a first surface 74, a second opposing surface 76, a first end region 78, and a second end region 80. The body 72 defines a channel 82 extending along a longitudinal axis 84 from the first end region 78 to the second end region 80. The device 70 further comprises a first inlet 86, a second inlet 88, a first outlet 90, and a second outlet 92, all in fluid communication with the channel 82. FIG. 6A is an exploded, cross-sectional perspective of the device 70 taken along line 6A of FIG. 5 when the device 70 is generated by stacking a plurality of layers together as shown in FIG. 6B. As shown in FIGS. 6A and 6B, the channel 82 is bifurcated at the first end region 78 by a first planar shelf 94 defined by the body 72, which keeps components that are introduced into the device 70 through the inlets 86, 88 separate. However, in some embodiments (not shown) there is only one inlet and no shelf to separate components. Also, the channel 82 is bifurcated at the second end region 80 by a second planar shelf 96 defined by the body 72, which keeps the components separated for collection through the outlets 90, 92 by way of a first collection channel 97 and a second collection channel 99, respectively.

The channel 82 of the device 70 includes a receiving or mixing region 98 near the first end region 78, a collection region 102 near the second end region 80, and a separation region 100 there between. Additionally, the channel 82 comprises a channel floor 104, two side walls 106 that extend longitudinally along the axis 84, and a channel ceiling 108. In various embodiments, the channel floor 104 and sides 106 are composed of a phantom material as described above. In various embodiments, at least the separation region 100 of the channel 82 has a rectangular cross-sectional geometry. Additionally, the separation region 100 of the channel 82 has a length L, a width W, and a height H that results in passing a large volume through the device. As described above, the channel 82 can have a cross-sectional aspect ratio (W:H) of from about 1:1 to about 50:1. In various embodiments, the length L is greater than about 20 mm or greater than about 100 mm. In other embodiments, the length L is from about 10 mm to about 100 mm, or from about 25 mm to about 75 mm. In yet other embodiments, the length L is about 10 mm, about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, or about 100 mm. In various embodiments, the width W is greater than about 5 mm, or greater than about 50 mm. In other embodiments, the width W is from about 5 mm to about 50 mm, or from about 20 mm to about 40 mm. In yet other embodiments, the width W is about 5 mm, about 10 mm, about 15 mm, about 20 mm, about 25 mm, about 30 mm, about 35 mm, about 40 mm, about 45 mm, or about 50 mm. In various embodiments, the height H is greater than about 0.5 mm, or greater than about 3 mm. In other embodiments, the height H is from about 0.5 mm to about 3 mm. In yet other embodiments, the height H is about 0.5 mm, about 1 mm, about 1.5 mm, about 2 mm, about 2.5 mm, or about 3 mm. The dimensions of the channel 82 allow for a high throughput of a mixture to be washed. Therefore, the device 70 can process blood compositions, mixtures, or suspensions at a rate of about 10 mL/min to about 30 mL/min, or at a rate from about 20 mL/min to about 25 mL/min. In one embodiment, the device 70 processes blood compositions, mixtures, or suspensions at a rate of about 22.5 mL/min. Accordingly, a unit of blood, having a volume of from about 400 mL to about 500 mL, combined with from about 0.5 L to about 3 L of wash solution can be processed in from about 30 min to about 350 min. In one embodiment, the device 70 can process a volume of 450 mL in about 20 min. However, the device 70 can accommodate and process a volume of from about 1 mL to about 20 L, wherein about 20 L can be processed in about 12 hrs, in about 13 hrs, or in about 14 hrs.

Additionally, the device 70 comprises a first wave component 110 positioned adjacent and parallel to the channel 82 and a second wave component 112 positioned adjacent and parallel to the channel 82, such that the channel 82 is positioned between the first and second wave components 110, 112. In various embodiments, the separating region 100 of the channel 82 is positioned between the first and second wave components 110, 112. The first wave component 110 and the second wave component 112 are individually either a wave generator or a reflective material or reflective surface or layer. However, when one of the wave components 110, 112 is a reflective material or reflective surface or layer, the other wave component 110, 112 is a wave generator. In embodiments where the second wave component 112 is a reflective surface, the reflective surface can be the second surface 76 of the device 70, or it can be a reflective film, sheet, slide, or membrane coupled to the second surface 76. As discussed further below regarding systems of the present technology, in some embodiments the first wave component 110 is an electrical contact that couples to a wave generator on a base unit. Therefore, when the first wave component 110 is a wave generator or an electrical contact, the second wave component 112 is either a second wave generator or a reflective surface or layer or material.

When the device 70 is activated, a SAW is generated between the first wave component 110 and the second wave component 112, whereby a pressure node 114 (see FIG. 7B) associated with the SAW is located within the separation region 100 of the channel 82. In various embodiments, the SAW is generated from the wave components 86, 88 operating at a low frequency range of from about 300 kHz to about 1000 kHz, or from about 400 kHz to about 600 kHz, or from about 450 kHz to about 500 kHz, in order to isolate components from a multicomponent mixture in the channel 62 with such a large volume. Even though this low frequency range results in a low pressure gradient, surprisingly, component isolation is achieved. In other embodiments, not shown in FIG. 4, the device 70 further comprises third and fourth wave components as or on opposing sides of the device 70 such that the third and fourth wave components generate a second SAW orthogonal to the SAW generated by the first and second wave components 110, 112, wherein the second SAW provides a second pressure node located in the separation region 100 of the channel 82.

The device 70 can be manufactured by any means known in the art, including, for example, injection molding, compression molding, or 3-dimensional printing (3-D printing). In some embodiments, as shown in FIG. 6B, the device 70 is manufactured by stacking together a plurality of layers 116a-116h, wherein each layer is bonded to an adjacent layer with an adhesive. With the optional exception described below in regard to the layer 116g, the layers 116a-116h are composed of any material known in the art. Non-limiting examples of materials for the layers 116a-116h include plastics, such as polyethylene terephthalate (PET) acrylics, such as poly(methyl methacrylate) (PMMA), and glasses. Combining the layers 116a-116h results in the device 70 with the cross-sectional geometry shown in FIG. 6A. The layer 116g has two longitudinal protrusions 118 that form the two side walls 106 of the channel 82. In various embodiments, the layer 116g is composed of a phantom material (as described above) that mimics how acoustic waves travel through water to provide the device 70 with the channel 82 having phantom side walls 106 and a phantom floor 104. In some embodiments, not shown in FIG. 6A or 6B, the first wave component 110 is coupled to a bottom surface 120 of the layer 116g and the layer below it, layer 116h, is optional. In other embodiments, the first wave component 110 is coupled to a bottom surface 122 of the layer 116h. A first layer 116a can either be composed of a reflective material or the second wave component 112 can be coupled to a surface 76 of the layer 116a. Moreover, the first layer 116a can be composed of a phantom material in various embodiments.

Figure 7A:
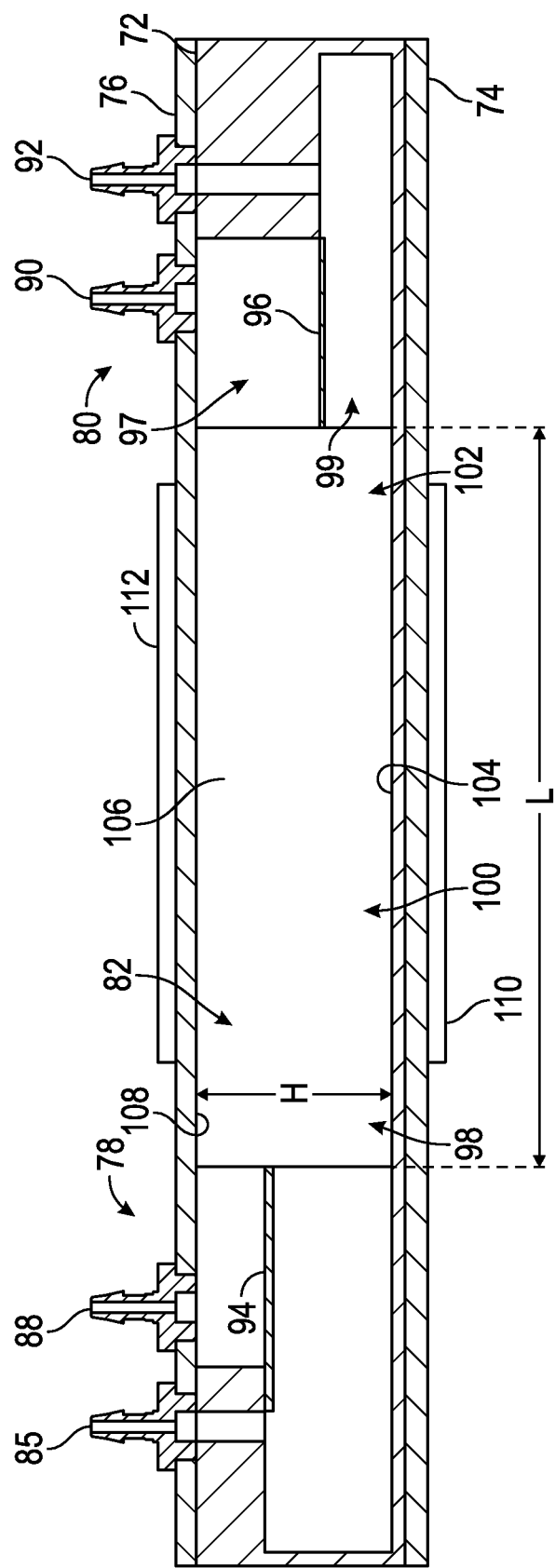
FIG. 7A is a cross-section perspective of the device of FIG. 5 that does not include a plurality of layers.

FIG. 7 is a cross-sectional illustration of the device 70 when the device 70 is manufactured by a means other than by stacking together a plurality of layers, such as by injection molding, compression molding, or 3-D printing. The components of FIG. 7 are the same as those shown in FIGS. 6A and 6B, but the dimensions may be slightly different.

Figure 7B:
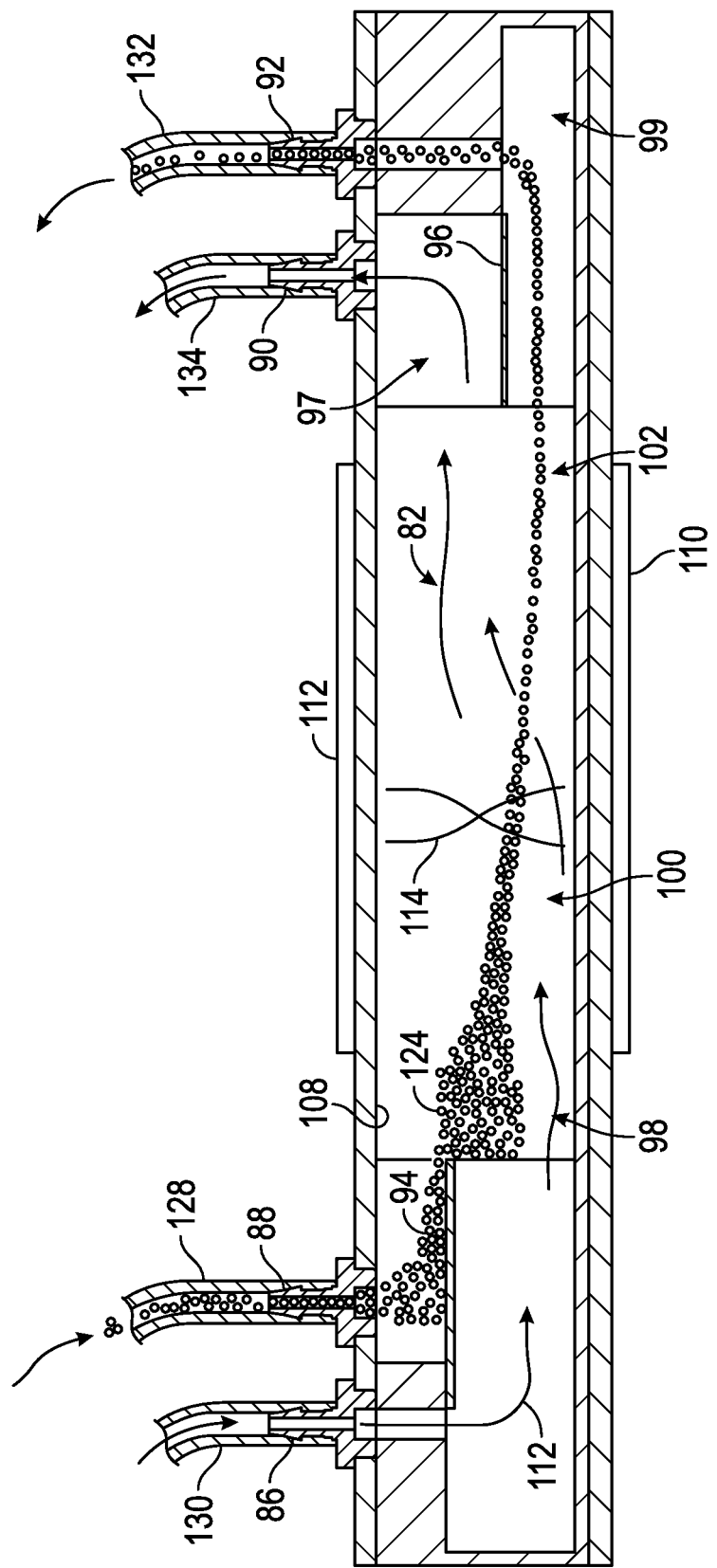
FIG. 7B is a cross-section perspective of the device of FIG. 7A, wherein cells and wash material are flowing through the device.

With reference to FIGS. 5-7B, the device 70 is configured to wash a multicomponent mixture. As described above, in various embodiments the multicomponent mixture comprises red blood cells 124 or red blood cells 124 and a rejuvenation solution. The multicomponent mixture is introduced to the device 70 through a first conduit coupled to an inlet 86, 88. As shown in FIG. 7B, a first conduit 128 is coupled to the second inlet 88. Likewise, a wash material 126 is introduced to the device 70 through a second conduit coupled to the inlet 86, 88 that is not coupled to the first conduit 128. As shown in FIG. 7, a second conduit 130 is coupled to the first inlet 86. Flow of the multicomponent mixture comprising red blood cells 124 and the wash material 126 can be established, by pumps, such as peristaltic pumps, optionally coupled to pulse dampeners or pulse suppressors. Examples of suitable pumps, pulse dampeners, and pulse suppressors that can be used for any embodiments provided herein are described in U.S. Patent Publication No. 2015/0111195, Hamman et al., published on Apr. 23, 2015, which is incorporated herein by reference. Upon entry into the device 70, the multicomponent mixture comprising red blood cells 124 and the wash material 126 are mixed together at the receiving or mixing region 98 of the channel 82. In other embodiments, the multicomponent mixture and washing material are combined prior to be introduced into the device 70. In such embodiments, the device 70 may have a single input, as described above or the multicomponent mixture and wash material can be delivered into the device by either inlet 86, 88 of the device 70.

Referring again to FIGS. 5-7B, as the multicomponent mixture comprising red blood cells 124 and the wash material 126 flow through the channel 82, they interact with a pressure node 114, generated by the wave components 110, 112, in the separation region 100 of the channel 82. In various embodiments, the pressure node 114 is located at or near the channel ceiling 108 and/or the channel floor 104, such that an antinode is positioned at a location to which the red blood cells 124 are directed. Although the wave components 110, 112 are shown positioned in the middle of the first and second surfaces 74, 76 in FIGS. 5, 6A, 7A, and 7B, in some embodiments (as discussed above), the wave components 110, 112 are positioned near the outlets 90, 92, such that a strong pressure wave pushes the cells 124 towards the collection channel 99 easier and with less power; rather than aligning the cells 124 the length of the channel 82. The pressure node 114 pushes, forces, isolates, or moves a component of the multicomponent mixture, such as the red blood cells 124, adjacent to the shelf 96 and into the second collection channel 99 while the remainder of the multicomponent mixture and wash material 126 flow to the first collection channel 97. The shelf 96 is thin and rigid so as to minimize turbulence within the channel 82. The component pushed, forced, isolated, or moved to the second collection channel 99 is collected through a third conduit 132 coupled to the second outlet 92 and the remaining materials are collected through a fourth conduit 134 coupled to the first outlet 90.

In various embodiments, chips are designed so have a particular spacial orientation, such as in systems (as described below) in which the devices are placed in a base unit. Thus, the gravity may have an effect on the flow of materials, such as cellular materials, through the chip. In some embodiments, the outlet of the chip is oriented lower than the inlet (i.e., at a location at a position lower than the inlet relative to the vertical axis of the chip, it being understood that the inlet and outlet are substantially at opposing ends of the chip relative to the orthogonal horizontal axis of the chip). In other embodiments, the outlet of the device is oriented higher than inlet. For example, FIGS. 6B and 7B show red blood cells 124 flowing downward to the second collection channel 99. In other embodiments the pressure antinode is located such that the component is forced upward to the first collection channel 97. In such embodiments, the red blood cells 124 are preferably introduced through the first inlet 86 and the wash material 126 is introduced through the second inlet 88. As the red blood cells 124 flow against the channel floor 104, the wash material 126 contacts an upper surface of the flow of red blood cells 124. When the red blood cells 124 interact with the nodes of a SAW generated between the wave components 110, 112, the red blood cells 124 are forced upward, against gravity, through the wash material 126 and isolated at the first collection channel 97 as washed red blood cells 124. The isolated and washed red blood cells are then collected through the first outlet 90 and the remaining materials are collected through the second outlet 92. Another example of such an embodiment, where cells are forced upward against gravity by a node of a SAW is shown in FIG. 12, which is described in more detail below.

Figure 8:
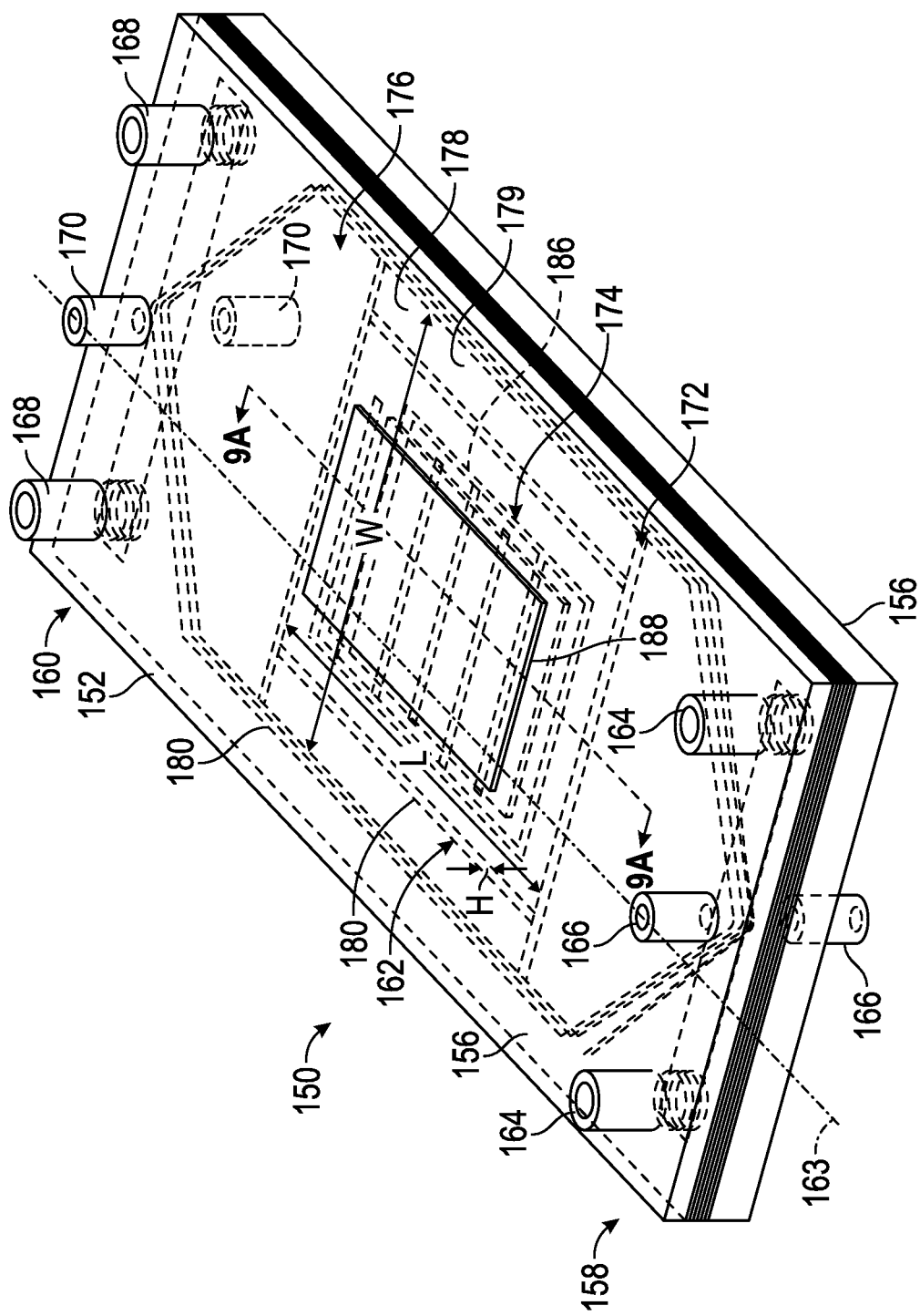
FIG. 8 is a perspective illustration of a device according to the present technology.
Figure 9A:
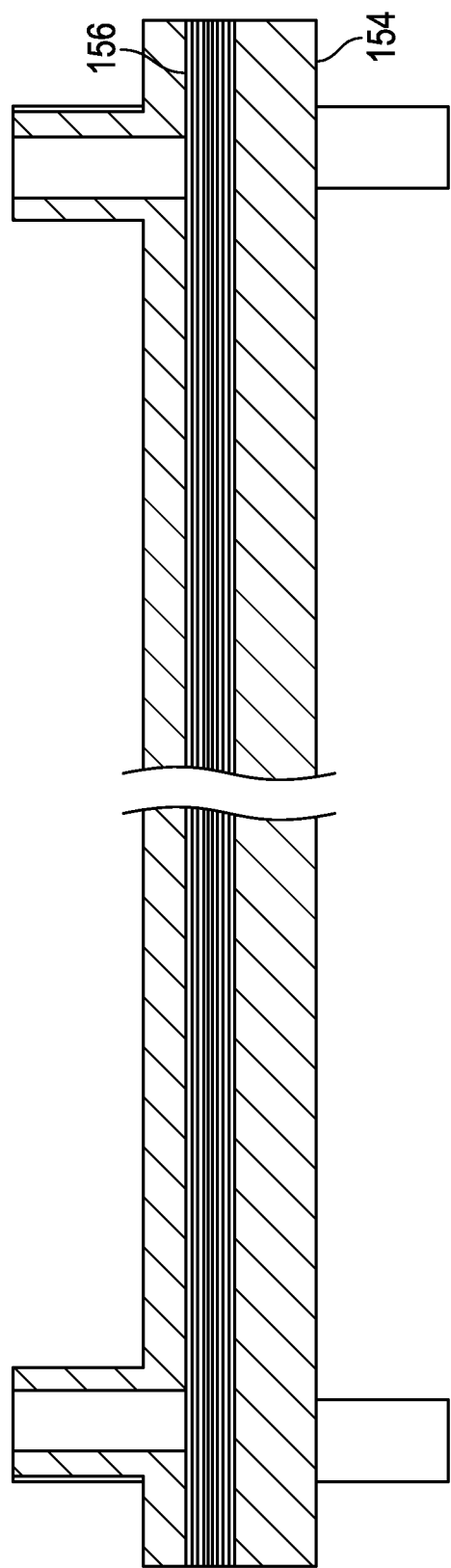
FIG. 9A is a cross-sectional perspective of the device of FIG. 8 taken along line 9A.
Figure 9B:
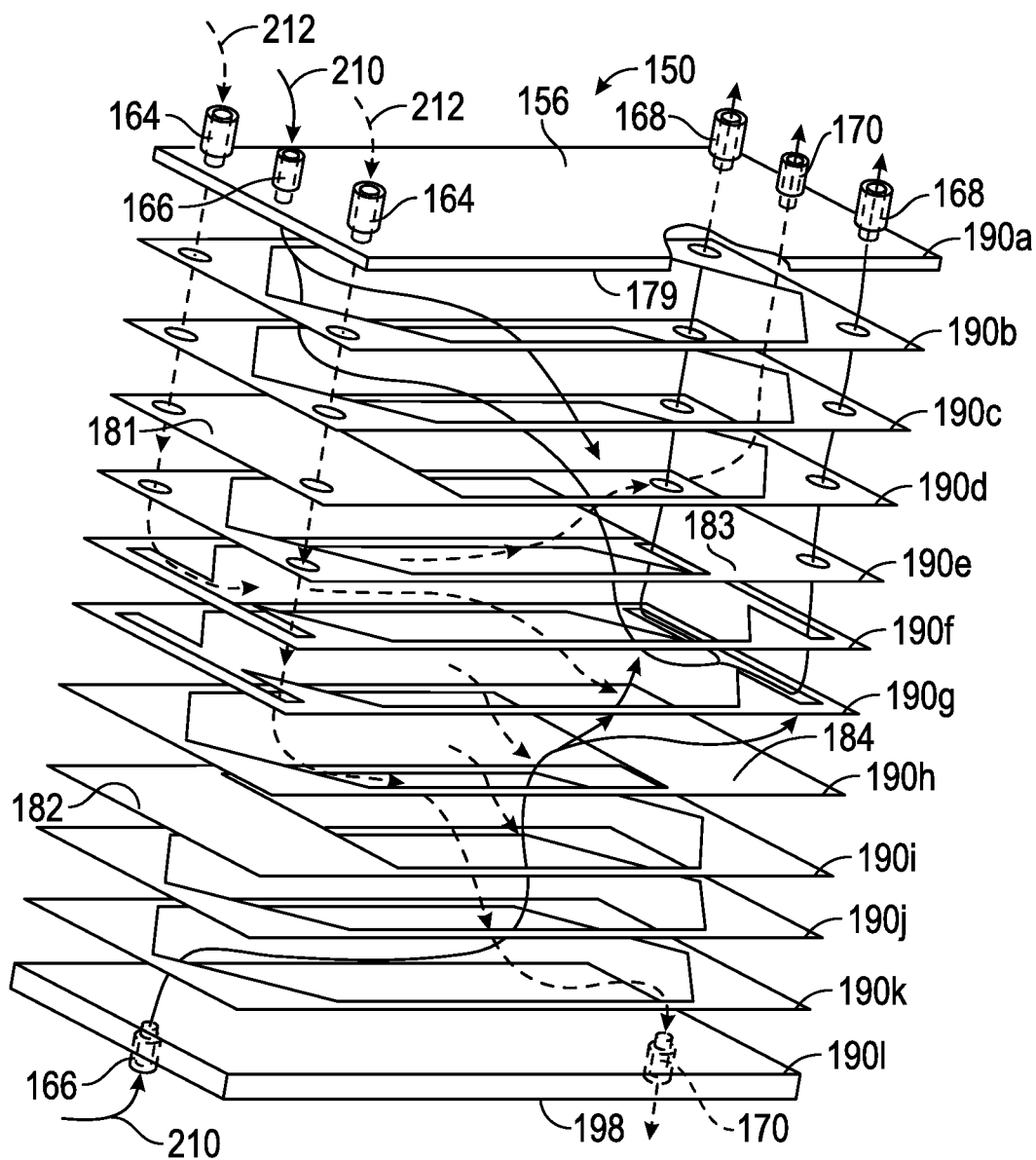
FIG. 9B is an exploded view of a plurality of layers that combine to form the device shown in FIGS. 8 and 9A.
Figure 10:
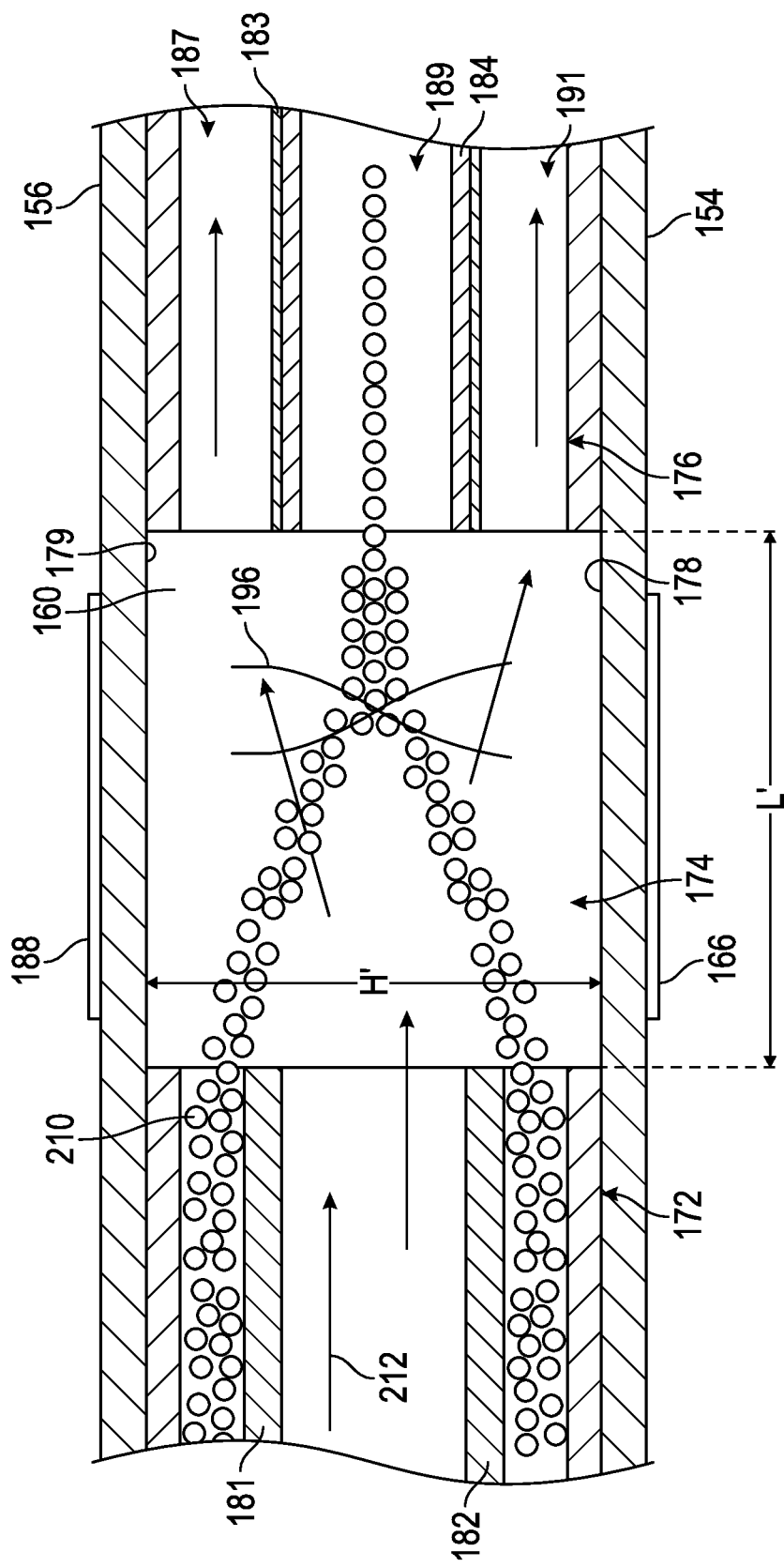
FIG. 10 is a cross-section perspective of the device of FIG. 8 that does not include a plurality of layers.

With reference to FIGS. 8-10, the present technology provides another device 150 for washing a multicomponent mixture. The device 150 comprises a body 152 having a first surface 154, a second opposing surface 156, a first end region 158, and a second end region 160. The body 152 defines a channel 162 extending along a longitudinal axis 163 from the first end region 158 to the second end region 160. The device 150 further comprises a first pair of inlets 164, a second pair of inlets 166, a first pair of outlets 168, and a second pair of outlets 170, all in fluid communication with the channel 162. FIG. 10 is an exploded cross-sectional perspective of the device 150 taken along line 9A of FIG. 8 when the device 150 is generated by stacking a plurality of layers together as shown in FIG. 9B. As shown in FIGS. 9A and 9B, the channel 162 is trifurcated at the first end region 158 by a first shelf 181 defined by the body 152 and a second shelf 182 defined by the body 152, which keeps components that are introduced into the device 150 through the pairs of inlets 164, 166 separate. Also, the channel 162 is trifurcated at the second end region 160 into a first collection channel 187, a second collection channel 189, and a third collection channel 191 by a third shelf 183 defined by the body 152 and fourth shelf 184 defined by the body 152, wherein the first collection channel 187 is located between the second surface 156 and the third shelf 183, the second collection 189 channel is located between the third and fourth shelves 183, 184, and the third collection channel 191 is located between the fourth shelf 184 and the first surface 154. The collection channels 187, 189, 191, keep the components separated for collection through the pairs of outlets 168, 170, such that the second collection channel 189 is in fluid communication with the first pair of outlets 168 and the first and third collection channels 187, 191 are in fluid communication with the second pair of outlets 170.

The channel 162 of the device 150 includes a receiving or mixing region 172 near the first end region 158, a collection region 176 near the second end region 160, and a separation region 174 there between. Additionally, the channel comprises a channel floor 178, two side walls 180 that extend longitudinally along the axis 163, and a channel ceiling 179. In various embodiments, the channel floor 178 and sides 180 are composed of a phantom material as described above. In various embodiments, at least the separation region 174 of the channel 162 has a rectangular cross-sectional geometry. Additionally, the separation region 174 of the channel 162 has a length L', a width W', and a height H' that results in passing a large volume through the device 150. As described above, the channel 162 can have a cross-sectional aspect ratio (W':H') of from about 1:1 to about 50:1. In various embodiments, the length L' is greater than about 20 mm or greater than about 100 mm. In other embodiments, the length L' is from about 10 mm to about 100 mm, or from about 25 mm to about 75 mm. In yet other embodiments, the length L' is about 10 mm, about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, or about 100 mm. In various embodiments, the width W' is greater than about 5 mm, or greater than about 50 mm. In other embodiments, the width W' is from about 5 mm to about 50 mm, or from about 20 mm to about 40 mm. In yet other embodiments, the width W' is about 5 mm, about 10 mm, about 15 mm, about 20 mm, about 25 mm, about 30 mm, about 35 mm, about 40 mm, about 45 mm, or about 50 mm. In various embodiments, the height HP is greater than about 0.5 mm, or greater than about 3 mm. In other embodiments, the height H' is from about 0.5 mm to about 3 mm. In yet other embodiments, the height H' is about 0.5 mm, about 1 mm, about 1.5 mm, about 2 mm, about 2.5 mm, or about 3 mm. The dimensions of the channel 62 allow for a high throughput of a mixture to be washed. Therefore, the device 150 can process blood compositions, mixtures, or suspensions at a rate of about 10 mL/min to about 30 mL/min, or at a rate from about 20 mL/min to about 25 mL/min. In one embodiment, the device 150 processes blood compositions, mixtures, or suspensions at a rate of about 22.5 mL/min. Accordingly, a unit of blood, having a volume of from about 400 mL to about 500 mL, combined with from about 0.5 L to about 3 L of wash solution can be processed in from about 30 min to about 350 min. In one embodiment, the device 150 can process a volume of 450 mL in about 20 min. However, the device 150 can accommodate and process a volume of from about 1 mL to about 20 L, wherein about 20 L can be processed in about 12 hrs, in about 13 hrs, or in about 14 hrs.

Additionally, the device 150 comprises a first wave component 186 positioned adjacent to the channel 162 on or near the first side 154 of the device 150 and a second wave component 188 positioned adjacent to the channel 162 on or near the second side 156 of the device 150 such that the channel 162 is positioned between the first and second wave components 186, 188. In various embodiments, the separation region 174 of the channel 162 is positioned between the first and second wave components 186, 188. Unless described otherwise, the first wave component 186 and the second wave component 188 are individually either a wave generator or a reflective material or reflective surface. However, when one of the wave components 186, 188 is a reflective material or reflective surface, the other wave component 186, 188 is a wave generator. Therefore, at least one of the wave components 186, 188 is a wave generator. In embodiments where the second wave component 188 is a reflective surface, the reflective surface can be the second surface 156 of the device 150, or it can be a reflective film, sheet, slide, or membrane. As discussed further below, in some embodiments the first wave component 186 is an electrical contact that couples to a wave generator on a base unit. Therefore, when the first wave component 186 is a wave generator or an electrical contact, the second wave component 188 is either a second wave generator or a reflective surface or material. When the device 150 is activated, a SAW is generated between the first wave component 186 and the second wave component 188, whereby a pressure node 196 (see FIG. 10) associated with the SAW is positioned within the separation region 174 of the channel 162. In various embodiments, the SAW is generated from the wave components 186, 188 operating at a low frequency range of from about 300 kHz to about 1000 kHz, or from about 400 kHz to about 600 kHz, or from about 450 kHz to about 500 kHz, in order to isolate components from a multicomponent mixture in the channel 162 with such a large volume. Even though this low frequency range results in a low pressure gradient, surprisingly, component isolation is achieved. In other embodiments, not shown in FIG. 8, the device 150 further comprises third and fourth wave components as or on opposing sides of the device 150 such that the third and fourth wave components generate a second SAW orthogonal to the SAW generated by the first and second wave components 186, 188, wherein the second SAW provides a second pressure node located in the separation region 174 of the channel 162.

Figure 11:
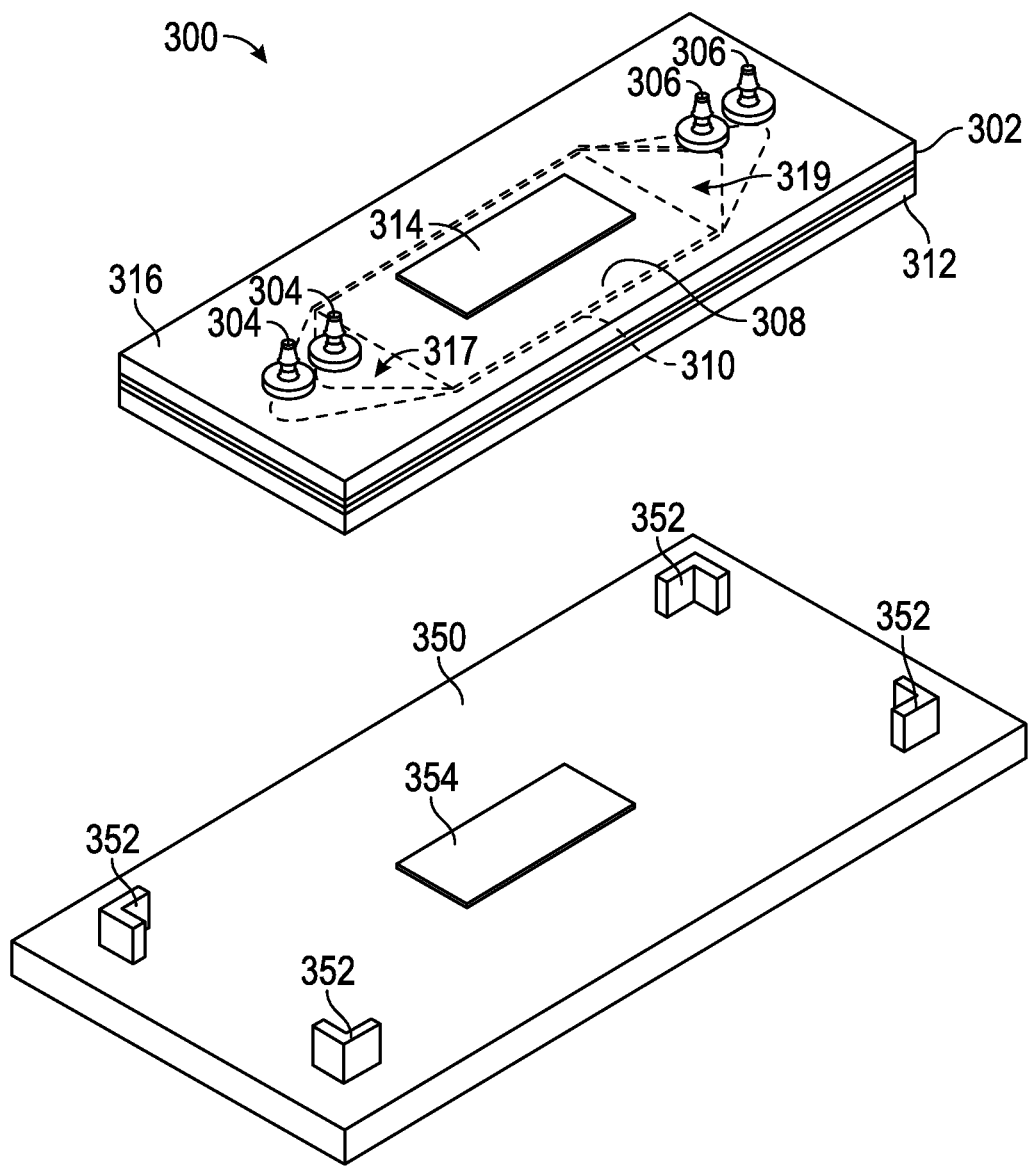
FIG. 11 is a schematic illustration of a system for washing multicomponent mixtures according to the present technology.

The device 150 can be manufactured by any means known in the art, including, for example, injection molding, compression molding, or 3-dimensional printing (3-D printing). In some embodiments, as shown in FIG. 11, the device 150 is manufactured by stacking together a plurality of layers 190a-190l, wherein each layer is bonded to an adjacent layer with an adhesive. With the optional exception described below in regard to a phantom layer, the layers 190a-190l are composed of any material known in the art. Non-limiting examples of materials for the layers 190a-190l include plastics, such as polyethylene terephthalate (PET) acrylics, such as poly(methyl methacrylate) (PMMA), and glasses. Combining the layers 190*a*-190*l* results in the device 150 with the cross-sectional geometry shown in FIG. 10. Optionally, an optional layer equivalent to layer 90*g* of FIG. 7, but configured to provide communication between layer 190*k* and the second input 166 and second output 170, is positioned between layer 190*k* and 190*l* and has two longitudinal protrusions that form the two side walls 180 of the channel 162. In various embodiments, the optional layer is composed of a phantom material that mimics how acoustic waves travel through water to results in the device 150 with the channel 162 having phantom side walls 180 and a phantom floor 178. In some embodiments, not shown in FIG. 11, the first wave component 186 is coupled to a bottom surface of the optional layer. In other embodiments, the first wave component 186 is coupled to a bottom surface 198 of the layer 190*l*. In yet other embodiments, layer 190*l* is composed of a phantom material and comprises two longitudinal protrusions that form the two side walls 180 of the channel 162. In such embodiments, the first wave component 186 is coupled to the bottom surface 198 of the layer 190*l*. A first layer 190*a* can either be composed of a reflective material or the second wave component 188 can be coupled to the second surface 156 of the layer 190*a*. Moreover, the first layer 190*a* is composed of a phantom material in various embodiments.

FIG. 10 is a cross-sectional illustration of the device 150 when the device 150 is manufactured by a means other than by stacking together a plurality of layers, such as by injection molding, compression molding, or 3-D printing. The components of FIG. 10 are the same as those shown in FIGS. 9A and 9B, but the dimensions may be slightly different.

With reference to FIGS. 8-10, the device 150 is configured to wash a multicomponent mixture. As described above, in various embodiments the multicomponent mixture comprises red blood cells 210 or red blood cells 210 and a rejuvenation solution. The multicomponent mixture comprising red blood cells 210 is introduced to the device 150 through a pair of first conduits coupled to the pair of second inlets 166. Likewise, a wash material 212 is introduced to the device 150 through a pair of second conduits coupled to the pair of first inlets 164. Flow of the multicomponent mixture 210 and the wash material 212 can be established, by pumps, such as peristaltic pumps, optionally coupled to pulse dampeners or pulse suppressors, as described above. Upon entry into the device 150, the multicomponent mixture 210 and the wash material 212 are mixed together at the receiving or mixing region 172 of the channel 162. In other embodiments, the multicomponent mixture comprising red blood cells 210 and the washing material 212 are combined prior to be introduced into the device 150 to generate a pre-mixed composition. In such embodiments, the device 150 may have a single input, as described above, or the pre-mixed composition can be delivered into the device 150 by any inlet or combination of inlets 164, 166. Referring again to FIGS. 8-10, as the multicomponent mixture comprising red blood cells 210 and the wash material 212 flows through the channel 162, they interact with a pressure node 196, generated by the wave components 186, 188, in the separation region 174 of the channel 162. In various embodiments, the pressure node 196 is located at or near the channel ceiling 179 and/or the channel floor 178, such that an antinode is positioned at a location to which the red blood cells 210 are directed. As discussed above, although the wave components 186, 188 are shown positioned in the middle of the first and second surfaces 154, 156 in FIGS. 8 and 10, in some embodiments, the centers of the wave components 186, 188 are positioned near to the outlets 168, 170, such that a strong pressure wave pushes the cells 210 towards the collection channel 189 easier and with less power; rather than aligning the cells 210 the length of the channel 162. The pressure node 196 pushes, forces, isolates, or moves a component of the multicomponent mixture, such as red blood cells, between the third and fourth shelves 183, 184 and into the second collection channel 189 while the remainder of the multicomponent mixture and wash material flow into the first and third collection channels 187, 191. The third and fourth shelves 183, 184 are thin and rigid so as to minimize turbulence within the channel 162. The component pushed, forced, isolated, or moved into the second collection channel 180 is collected through a third pair of conduits coupled to the first pair of outlets 168 and the remaining materials are collected through a fourth pair of conduits coupled to the second pair of outlets 170.

With further reference to FIG. 15, the present technology provides another device 600 for washing a multicomponent mixture. The device 600 comprises a separation chip 602 having a body 604. The body 604 has a top surface 606 and an opposing bottom surface 608. Additionally, the body 604 defines an upper inlet channel 610 and a lower inlet channel 612 that merge into a first end 614 of a separation channel 616 due to an incline path of the lower inlet channel 612. The separation channel 616 has a channel ceiling 618 and a channel floor 620. The separation channel 616 bifurcates at a second end 622 into an upper outlet channel 624 and a lower outlet channel 626, wherein the lower outlet channel 626 has a declined path relative to the separation channel 616. A first wave component 628 is positioned on the top surface 606 of the chip 602 and a second wave component 630 is positioned on the bottom surface 608 of the chip 602. The first wave component 628 and the second wave component 630 are individually either a wave generator or a reflective material or reflective surface or layer. However, when one of the wave components 628, 630 is a reflective material or reflective surface or layer, the other wave component 628, 630 is a wave generator. The first and second wave components 628, 630 have a center or central region represented by a dotted line axis 632. As discussed above, the wave components 628, 630 are positioned on the respective surfaces 606, 608 of the chip 602 such that their center or central power generating region, defined by a first end point 650 and a second end point 651, is aligned with the second end 622 of the separation channel 616 prior to the separation channel's 616 bifurcation into the upper and lower outlet channels 624, 626. In some embodiments, it has been found that this alignment can result in high separation efficiency because a resulting SAW is strongest in a region between the center regions of the wave components 628, 630 and because cells do not have to be suspended throughout the whole length of the separation channel 616 as discussed further below. However, in other embodiments, the wave components 628, 630 are positioned relative to other sections of the separation channel 616, with the proviso that the separation channel 616 is positioned between the first and second wave components 628, 630.

The device 600 is configured to wash a multicomponent mixture comprising cells 634. As described above, in various embodiments the multicomponent mixture comprises red blood cells or red blood cells and a rejuvenation solution. The multicomponent mixture comprising red blood cells 634 is introduced to the device 600 through a lower inlet port 636 that is in fluid communication with the lower inlet channel 612. Likewise, a wash material 638 is introduced to the device 600 through an upper inlet port 640 that is in fluid communication with the upper inlet channel 610. Flow of the multicomponent mixture 634 and the wash material 638 can be established, by pumps, such as peristaltic pumps, optionally coupled to pulse dampeners or pulse suppressors, as described above. As the multicomponent mixture 634 and the wash material 638 merge at the separation channel, the multicomponent mixture 634 flows adjacent to the channel floor 620 and the wash material 638 flows adjacent to the channel ceiling 618. As such, the wash material 638 flows over the multicomponent mixture 634 to create an interface between the wash material 638 and the multicomponent mixture 634. There is little or no mixing between the wash material 638 and the multicomponent mixture 640 near the first end 614 of the separation channel. The first and second wave components 628, 630 generate a SAW with an antinode positioned near the upper outlet channel 624. As the multicomponent mixture comprising cells 634 and the wash material 638 flow relative to the SAW at the second end 622 of the separation channel 616, pressure nodes pushes, forces, isolates, or moves the cells 634 toward the antinode positioned near the upper outlet channel 624. Accordingly, the cells 634 are forced upward through the wash material 638 and toward the upper outlet channel 624, whereby the cells 634 are washed and cleaned. This movement of the cells 634 displaces the wash material 638 and remaining components of the initial multicomponent mixture comprising cells 634 into the lower outlet channel 644. Red blood cells 634 that are washed and clean can be collected at an upper outlet port 642 that is in fluid communication with the upper outlet channel 624 and remaining wash material 638 along with other components, such as, for example, rejuvenation solution, can be collected at a lower outlet port 644 that is in fluid communication with the lower outlet channel 626.

Systems

The present technology provides systems for separating of cells from a multicomponent fluid, comprising a device of the present technology (as described above) and a base unit that facilitates the function of the device. In some embodiments, the device is a disposable chip, operable for a limited number of uses (e.g., a single use). Preferably in such embodiments the base unit comprises components that are operable for multiple uses.

An exemplary system 300 is shown in FIG. 11. The system comprises a disposable separation device 302 and base unit 350. Any separation device described herein, including the device 70 of FIG. 5 and the device 150 of FIG. 8 can be used as the separation device 302. In general, the separation device 302 comprises inlets 304, outlets 306, a channel 308, an optional first wave component 310 coupled to a first surface 312, and a second wave component 314 coupled to a second opposing surface 316, wherein the inlets 304 are in fluid communication with a first end of the channel 317 and the outlets 306 are in fluid communication with a second end of the channel 319. The optional first wave component 310 can be a wave generator. The second wave component 314 can be a wave generator or a reflective material or surface or layer.

The base unit 350 comprises at least one of a plurality of coupling members 352 and a third wave component 354. The coupling members can be any coupling members known in the art. Non-limiting examples of connecting members include snaps, clips, clasps, screws, adhesives, fasteners, etc. The third wave component 354 is either a wave generator or an electrical contact. In embodiments where the first wave component 310 of the disposable separation device 302 is a wave generator, the third wave component 354 is an electrical contact. In one embodiment the disposable separation device 302 comprises a first wave component 310, which is a wave generator. In such embodiments, the third wave component 354 of the base unit 350 is an electrical contact. The coupling members 352 are then configured to couple and hold the disposable separation device 302 to the base unit 350 such that the wave generator of the disposable separation device 302 contacts and communicates with the electrical contact. In another embodiment, the disposable device 302 does not comprise a first wave component 310. In this embodiment, the third wave component 354 of the base unit 350 is a wave generator. The snaps 352 are then configured to snap the disposable separation device 302 to the base unit 350 such that the separation channel 308 is positioned between the wave generator on the base unit 350 and the second wave component 314 of the disposable separation device 302. Nonetheless, in all embodiments a SAW is generated in the disposable separation device 302 with power provided by the base unit 350.

The disposable separation device 302 can be prepackaged and sterilized. When ready for use, the disposable separation device 302 is removed from the packaging and snapped onto the base unit 350. A wash material is then pumped through the device and the base unit is activated to generate an SAW. A multicomponent mixture, such as a red blood cell composition, is then pumped through the separation device 302, wherein the blood is washed and separated from undesired components.

Methods

The present technology provides devices, systems, and methods for separating a target component from a multicomponent fluid. For example, the target component may be red blood cells or other cells. In various embodiments, the multicomponent fluid comprises a physiologically-acceptable carrier for the target component, such as saline or plasma. Methods include those comprising separating the red blood cells from one more second components of the multicomponent fluid. In some embodiments, the second component comprises at least a portion of the carrier; in some embodiments, the second component comprises essentially all of the carrier. The second component may be used in other processes, or may be discarded. In some embodiments wherein the target material is red blood cells, the second component comprises cells and cell debris, such as white blood cells, platelets, dead cells, or cell debris.

In various embodiments, the present technology provides methods for washing red blood cells that have been suspended in a storage solution or other carrier that is not suitable for administration to a human or other animal in a transfusion. In such methods, the red blood cells are substantially removed from storage solution, and resuspended in a wash solution in a device of the present technology.

For example, before transfusions, red blood cells are often rejuvenated with a rejuvenation or enhancement solution, such as Rejuvesol® red blood cell processing solution commercialized by Citra Labs, LLC (Braintree, Mass.). Such enhancement solutions and methods of use are described in U.S. Pat. No. 9,066,909, Alan Gray, issued Jun. 30, 2015; U.S. Patent Publication No. 2014/0212400, Alan Gray published Jul. 31, 2014, and U.S. Patent Publication No. 2014/0212397, Alan Gray et al., published Jul. 31, 2014, incorporated by reference herein. After rejuvenation, the red blood cells are washed with a wash solution, such as water, saline, dextrose, saline with 5% dextrose, phosphate buffered saline, and other wash liquids to remove excess rejuvenation solution from the red blood cells. Therefore, the rejuvenation solution and/or the wash solution need to be removed from the red blood cells prior to transfusion.

In some embodiments, methods for washing a multicomponent fluid comprising cells comprises delivering, such as by pumping or flowing, a composition comprising cells and a wash material into a separation device comprising a separation channel having a receiving or mixing region, a separation region and a collection region. In various embodiments, the composition comprising cells is a composition comprising red blood cells. The composition may also comprise materials to be washed away from the cells, including other cell types, dead cells, cell debris, rejuvenation solution, or combinations thereof. The wash material is selected from the group consisting of water, saline, dextrose, saline with 5% dextrose, and phosphate buffered saline. The separation device can be any separation device described above.

The method also comprises mixing the composition comprising cells with the wash material. Mixing occurs when the composition comprising cells contacts the wash material in the receiving or mixing region of the channel. Alternatively, the composition comprising cells can be mixed with the wash material outside of the device to generate a pre-mixed composition. In such embodiments, the pre-mixed composition is delivered into the separation device. Then, the method comprises isolating or separating a component from the composition comprising cells. The component can be a desired type of cell, such as, for example, red blood cells. Isolating or separating a component comprises passing, such as by pumping or flowing, the composition comprising cells and the wash material relative to a pressure node generated by a SAW, wherein a pressure node associated with the SAW is located within the separation region of the channel. The SAW is generated by wave components operating at a frequency range of from about 300 kHz to about 1000 kHz, or from about 680 kHz to about 710 kHz.

After the component is isolated or separated, the method comprises collecting the component at an outlet of the device that is in fluid communication with the collection region of the channel. In embodiments where the composition comprising cells is a composition comprising red blood cells, the red blood cells can be washed and isolated by this method, and then transfused into a human or non-human subject in need thereof.

An exemplary embodiment of the present technology is depicted in FIG. 12. As shown, a wash material liquid stream 401 is introduced in the mixing region or chamber 405 of a device 400 that is operable to separate a component from a multi-component solution using standing acoustic waves, such as described above. Such devices and methods are also described in U.S. patent application Ser. No. 14/519,284, Leach et al., filed Oct. 21, 2014, and U.S. Provisional Patent Application Ser. No. 62/095,480, Abeskaron, filed Dec. 22, 2014, the disclosures of which are incorporated by reference herein.

In further reference to exemplary FIG. 12, a cellular component liquid stream 402, such as comprising red blood cells (RBC), is introduced into the region 405, in contact with the wash material liquid stream. Application of acoustic waves causes the red blood cells to be moved to the wash material stream, forming a washed component liquid stream 403. While, as depicted in FIG. 4, the cellular component liquid stream 402 is introduced to the mixing region 405 below the wash material liquid stream 401, the relative orientation of the streams may be varied, e.g., such that the cellular component liquid stream 402 may be introduced above the wash material liquid stream 401.

In various embodiments, the interfacial tension between the cellular component liquid stream and the wash material liquid stream is near zero. The interfacial tension may be controlled by selection of the components of the respective streams. For example, one or both of the density and viscosity of the streams may be adjusted by inclusion of an interfacial adjustment material is preferably biocompatible materials suitable for intravenous administration to a human or animal subject. For example, the wash material liquid may comprise dextrose, sucrose or hydrophilic polysaccharide polymers (e.g., dextran and Ficoll) so as to effect a desired density or viscosity. Preferably, the wash material liquid comprises salt, and is isotonic with the cellular component, so as to avoid damage to the cells (e.g., through osmotic shock). In some embodiments, the wash material liquid comprises sucrose. For example, the wash material may be an isotonic mixture of saline and sucrose, having a sucrose concentration of about 9.25%.

As shown in FIG. 13A, generating a standing wave with a node positioned in a channel of a device forces particles to align into a standard band. In contrast, FIG. 13E shows free floating particles in a channel. However, the thickness of the band shown in FIG. 13A can be manipulated or tightened by adjusting various parameters. Input offset voltage (Vos) is a parameter that define a differential DC voltage required between inputs of an amplifier, such as an operational amplifier (op-amp), to make the output zero (for voltage amplifiers, 0 V with respect to ground or between differential outputs, depending on the output type). When an input offset voltage is applied, the band of particles flowing through a channel is tighter, i.e., thinner, relative to the standard band shown in FIG. 13A. Another parameter that may be adjusted is phase shift or phase offset. This parameter creates a change in the initiation point of a waveform. As shown in FIG. 13C, when a phase shift or phase offset is applied, the band of particles flowing through a channel is tighter, i.e., thinner, relative to the standard band shown in FIG. 13A. Also, a user may employ a dithered or swept signal. This process generates a signal for several given frequencies over a given time interval. As shown in FIG. 13D, when a dithered or swept signal is applied, the band of particles flowing through a channel is tighter, i.e., thinner, relative to the standard band shown in FIG. 13A. Moreover, channel volume, hematocrit and flow rate can also be adjusted to increase efficiency.

NON-LIMITING DISCUSSION OF TERMINOLOGY

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The disclosure of all patents and patent applications cited in this disclosure are incorporated by reference herein.

The description and specific examples, while indicating embodiments of the technology, are intended for purposes of illustration only and are not intended to limit the scope of the technology. Equivalent changes, modifications and variations of specific embodiments, materials, compositions and methods may be made within the scope of the present technology, with substantially similar results. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "prefer" or "preferable" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein. Further, as used herein the term "consisting essentially of" recited materials or components envisions embodiments "consisting of" the recited materials or components.

A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for separating a cellular component from a multicomponent fluid, comprising:
   a body defining a channel having a first surface and a second surface opposite the first surface, the channel extending along a longitudinal axis from a first end to a second end, the channel including a mixing region proximate the first end and a collection region proximate the second end, the mixing region configured to facilitate mixing of the multicomponent fluid and a wash material into a mixture;
   a first acoustic wave generator coupled to the first surface closer to the second end of the channel than to the first end of the channel, the first acoustic wave generator configured to generate an acoustic wave having a wavelength; and
   a second acoustic wave propagating component coupled to the second surface,
   wherein the second surface is spaced an integer fractional multiple of the wavelength from the first surface and each integer factional multiple equals a number of pressure nodes within the channel.

2. The device of claim 1, wherein a central power generating region of the first acoustic wave generator is aligned with the second end of the channel and proximate a bifurcation region of the channel.

3. The device of claim 1, wherein the integer fractional multiple is 0.5 and the number of pressure nodes is 1.

4. The device of claim 1, wherein the first acoustic wave generator and the second wave propagating component are located proximate a midpoint of the channel.

5. The device of claim 1, wherein the body comprises a phantom material forming at least a portion of one or both of the first surface and the second surface, wherein the phantom material has acoustic properties similar to those of the multicomponent fluid and a thickness such that at least one of the pressure nodes is located proximate the phantom material.

6. The device of claim 1, further comprising a first inlet and a second inlet proximate the first end, the first inlet having a higher elevation than the second inlet.

7. The device of claim 6, further comprising a first outlet and a second outlet proximate the second end, the second outlet having a higher elevation than the first outlet.

8. The device of claim 7, wherein the first inlet is configured to receive the wash material and the second inlet is configured to receive a multicomponent mixture.

9. The device of claim 8, wherein the second outlet is arranged to receive the cellular component and the first outlet is arranged to receive the wash material.

10. The device of claim 1, wherein the channel has a cross-sectional width and height, wherein an aspect ratio of width:height is from about 1:11 to about 50:1, and the first acoustic wave generator produces waves having a frequency of from about 100 kHz to about 2000 kHz.

11. The device of claim 1, wherein, during use, an antinode is formed at approximately the center of the channel and a first pressure node is formed at the first surface and a second pressure node is formed at the second surface.

12. A device for separating a cellular component from a multicomponent fluid, comprising:
a body defining a channel having a first surface and a second surface opposite the first surface, the channel extending along a longitudinal axis from a first end to a second end, the channel defining a mixing region proximate the first end and a bifurcation region proximate the second end, wherein the mixing region is configured to facilitate mixing of the multicomponent fluid and a wash material;
a first acoustic wave generator coupled to the first surface closer to the second end than the first end of the channel, the first acoustic wave generator configured to generate an acoustic wave having a wavelength, the first acoustic wave generator having a central power generating region aligned proximate the bifurcation region; and
a second acoustic wave propagating component coupled to the second surface,
wherein the second surface is spaced from the first surface such that, during use, an antinode is formed at approximately the center of the channel and a first pressure node is formed at the first surface and a second pressure node is formed at the second surface.

13. The device of claim 12, wherein the body comprises a phantom material forming at least a portion of one or both of the first surface and the second surface, wherein the phantom material has acoustic properties similar to those of the multicomponent fluid and a thickness such that at least one of the pressure nodes is located proximate the phantom material.

14. The device of claim 12, wherein the first acoustic wave generator or the second wave propagating component is a resonator.

15. The device of claim 12, further comprising a first inlet and a second inlet proximate the first end, the first inlet having a higher elevation than the second inlet.

16. The device of claim 15, further comprising a first outlet and a second outlet proximate the second end, the second outlet having a higher elevation than the first outlet.

17. The device of claim 16, wherein the first inlet is configured to receive the wash material and the second inlet is configured to receive a multicomponent mixture.

18. The device of claim 17, wherein the second outlet is arranged to receive the cellular component and the first outlet is arranged to receive the wash material.

19. A method of separating a cellular component from cellular component liquid stream, comprising:
introducing the cellular component liquid stream and a wash material into an acoustic wave separation device having a channel extending along a longitudinal axis from a first end to a second end, the channel defining a mixing region proximate the first end, the channel defining a collection region proximate the second end, the collection region including a first outlet and a second outlet;
combining the cellular component liquid stream and the wash material in the mixing region such that the mixing region contains a composition of the cellular component liquid stream and the wash material;
producing a standing acoustic wave using an acoustic wave generator positioned closer to the second end of the channel than to the first end of the channel, the standing acoustic wave having a pressure node located proximate the bifurcation region thereby forcing the cellular component from the cellular component liquid stream; and
collecting the concentrated cellular component in the second outlet.

20. The method of claim 19, wherein the standing acoustic wave is a surface acoustic wave.

* * * * *